United States Patent
Wei et al.

(10) Patent No.: US 7,943,395 B2
(45) Date of Patent: May 17, 2011

(54) EXTENSION OF THE DYNAMIC DETECTION RANGE OF ASSAY DEVICES

(75) Inventors: Ning Wei, Roswell, GA (US); Rameshbabu Boga, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1463 days.

(21) Appl. No.: 10/718,997

(22) Filed: Nov. 21, 2003

(65) Prior Publication Data

US 2005/0112779 A1    May 26, 2005

(51) Int. Cl.
   *G01N 33/53* (2006.01)
(52) U.S. Cl. ........ 436/514; 436/518; 436/528; 436/501; 436/164; 436/169; 436/172; 436/807; 435/4; 435/7.1; 435/287.1; 435/287.2; 435/287.7; 422/55; 422/56; 422/61; 422/68.1; 422/82.05
(58) Field of Classification Search ............. 422/55, 422/56, 61, 68.1, 82.05; 435/4, 7.1, 287.1, 435/287.2, 287.7, 287.8, 288.7; 436/501, 436/518, 528, 164, 169, 172, 807
See application file for complete search history.

(56) References Cited

U.S. PATENT DOCUMENTS

| | | | |
|---|---|---|---|
| 1,366,241 A | 1/1921 | Burch | |
| 3,604,927 A | 9/1971 | Hirschfeld | |
| 3,700,623 A | 10/1972 | Keim | |
| 3,772,076 A | 11/1973 | Keim | |
| 3,835,247 A | 9/1974 | Soames | |
| 4,006,360 A | 2/1977 | Mueller | |
| 4,094,647 A | 6/1978 | Deutsch et al. | |
| 4,110,529 A | 8/1978 | Stoy | |
| 4,115,535 A | 9/1978 | Giaever | |
| 4,168,146 A | 9/1979 | Grubb et al. | |
| RE30,267 E | 5/1980 | Bruschi | |
| 4,210,723 A | 7/1980 | Dorman et al. | |
| 4,235,601 A | 11/1980 | Deutsch et al. | |
| 4,259,574 A | 3/1981 | Carr et al. | |
| 4,275,149 A | 6/1981 | Litman et al. | |
| 4,312,228 A | 1/1982 | Wohltjen | |
| 4,336,459 A | 6/1982 | Fay | |
| 4,341,957 A | 7/1982 | Wieder | |
| 4,363,874 A | 12/1982 | Greenquist | |
| 4,366,241 A | 12/1982 | Tom et al. | |

(Continued)

FOREIGN PATENT DOCUMENTS

EP    0073593 A1    3/1983

(Continued)

OTHER PUBLICATIONS

U.S. Appl. No. 10/325,429, filed Dec. 19, 2002, Wei, et al., Self-Calibrated Flow-Through Assay Devices.

(Continued)

*Primary Examiner* — Bao-Thuy L Nguyen
(74) *Attorney, Agent, or Firm* — Dority & Manning, P.A.

(57) ABSTRACT

A flow-through assay device for detecting the presence or quantity of an analyte residing in a test sample is provided. The device utilizes multiple detection zones, one of which is premised on "competitive" binding of the analyte and the other is premised on "sandwich" binding of the analyte. The present inventors believe that the combination of these zones may enable the detection of an analyte over extended concentration ranges.

9 Claims, 5 Drawing Sheets

U.S. PATENT DOCUMENTS

| | | | |
|---|---|---|---|
| 4,374,925 A | 2/1983 | Litman et al. | |
| 4,385,126 A | 5/1983 | Chen et al. | |
| 4,426,451 A | 1/1984 | Columbus | |
| 4,427,836 A | 1/1984 | Kowalski et al. | |
| 4,435,504 A | 3/1984 | Zuk et al. | |
| 4,441,373 A | 4/1984 | White | |
| 4,442,204 A | 4/1984 | Greenquist et al. | |
| 4,444,592 A | 4/1984 | Ludwig | |
| 4,446,232 A * | 5/1984 | Liotta | 435/7.93 |
| 4,477,635 A | 10/1984 | Mitra | |
| 4,480,042 A | 10/1984 | Craig et al. | |
| 4,533,499 A | 8/1985 | Clark et al. | |
| 4,533,629 A | 8/1985 | Litman et al. | |
| 4,534,356 A | 8/1985 | Papadakis | |
| 4,537,657 A | 8/1985 | Keim | |
| 4,537,861 A | 8/1985 | Elings et al. | |
| 4,540,659 A | 9/1985 | Litman et al. | |
| 4,552,458 A | 11/1985 | Lowne | |
| 4,561,286 A | 12/1985 | Sekler et al. | |
| 4,562,157 A | 12/1985 | Lowe et al. | |
| 4,586,695 A | 5/1986 | Miller | |
| 4,595,661 A | 6/1986 | Cragle et al. | |
| 4,596,697 A | 6/1986 | Ballato | |
| 4,614,723 A | 9/1986 | Schmidt et al. | |
| 4,632,559 A | 12/1986 | Brunsting | |
| 4,661,235 A | 4/1987 | Krull et al. | |
| 4,698,262 A | 10/1987 | Schwartz et al. | |
| 4,722,889 A | 2/1988 | Lee et al. | |
| 4,727,019 A | 2/1988 | Valkirs et al. | |
| 4,731,337 A | 3/1988 | Luotola et al. | |
| 4,742,011 A | 5/1988 | Blake et al. | |
| 4,743,542 A | 5/1988 | Graham, Jr. et al. | |
| 4,743,560 A | 5/1988 | Campbell et al. | |
| 4,776,944 A | 10/1988 | Janata et al. | |
| 4,791,310 A | 12/1988 | Honig et al. | |
| 4,806,312 A | 2/1989 | Greenquist | |
| 4,835,099 A | 5/1989 | Mize et al. | |
| 4,837,168 A | 6/1989 | de Jaeger et al. | |
| 4,842,783 A | 6/1989 | Blaylock | |
| 4,843,000 A | 6/1989 | Litman et al. | |
| 4,843,021 A | 6/1989 | Noguchi et al. | |
| 4,844,613 A | 7/1989 | Batchelder et al. | |
| 4,849,338 A | 7/1989 | Litman et al. | |
| 4,855,240 A | 8/1989 | Rosenstein et al. | |
| 4,857,453 A | 8/1989 | Ullman et al. | |
| 4,867,908 A | 9/1989 | Recktenwald et al. | |
| 4,877,586 A | 10/1989 | Devaney, Jr. et al. | |
| 4,877,747 A | 10/1989 | Stewart | |
| 4,877,965 A | 10/1989 | Dandliker et al. | |
| 4,889,816 A | 12/1989 | Davis et al. | |
| 4,895,017 A | 1/1990 | Pyke et al. | |
| 4,904,583 A | 2/1990 | Mapes et al. | |
| 4,916,056 A | 4/1990 | Brown, III et al. | |
| 4,917,503 A | 4/1990 | Bhattacharjee | |
| 4,920,045 A | 4/1990 | Okuda et al. | |
| 4,940,734 A | 7/1990 | Ley et al. | |
| 4,954,435 A | 9/1990 | Krauth | |
| 4,956,302 A | 9/1990 | Gordon et al. | |
| 4,963,498 A | 10/1990 | Hillman et al. | |
| 4,973,670 A | 11/1990 | McDonald et al. | |
| 4,978,625 A | 12/1990 | Wagner et al. | |
| 4,980,298 A | 12/1990 | Blake et al. | |
| 4,992,385 A | 2/1991 | Godfrey | |
| 5,003,178 A | 3/1991 | Livesay | |
| 5,023,053 A | 6/1991 | Finlan | |
| 5,026,653 A | 6/1991 | Lee et al. | |
| 5,035,863 A | 7/1991 | Finlan et al. | |
| 5,051,162 A | 9/1991 | Kambara et al. | |
| 5,055,265 A | 10/1991 | Finlan | |
| 5,063,081 A | 11/1991 | Cozzette et al. | |
| 5,064,619 A | 11/1991 | Finlan | |
| 5,073,340 A | 12/1991 | Covington et al. | |
| 5,075,077 A | 12/1991 | Durley, III et al. | |
| 5,075,078 A | 12/1991 | Osikowicz et al. | |
| 5,076,094 A | 12/1991 | Frye et al. | |
| 5,096,671 A | 3/1992 | Kane et al. | |
| 5,114,676 A | 5/1992 | Leiner et al. | |
| 5,120,643 A | 6/1992 | Ching et al. | |
| 5,120,662 A | 6/1992 | Chan et al. | |
| 5,124,254 A | 6/1992 | Hewlins et al. | |
| 5,134,057 A | 7/1992 | Kuypers et al. | |
| 5,137,609 A | 8/1992 | Manian et al. | |
| 5,143,854 A | 9/1992 | Pirrung et al. | |
| 5,145,784 A | 9/1992 | Cox et al. | |
| 5,149,622 A | 9/1992 | Brown et al. | |
| 5,152,758 A | 10/1992 | Kaetsu et al. | |
| 5,156,953 A | 10/1992 | Litman et al. | |
| 5,166,079 A | 11/1992 | Blackwood et al. | |
| 5,179,288 A | 1/1993 | Miffitt et al. | |
| 5,182,135 A | 1/1993 | Giesecke et al. | |
| 5,185,127 A | 2/1993 | Vonk | |
| 5,196,350 A | 3/1993 | Backman et al. | |
| 5,200,084 A | 4/1993 | Liberti et al. | |
| 5,208,143 A | 5/1993 | Henderson et al. | |
| 5,208,535 A | 5/1993 | Nakayama et al. | |
| 5,221,454 A | 6/1993 | Manian et al. | |
| 5,225,935 A | 7/1993 | Watanabe et al. | |
| 5,234,813 A | 8/1993 | McGeehan et al. | |
| 5,235,238 A | 8/1993 | Nomura et al. | |
| 5,238,815 A | 8/1993 | Higo et al. | |
| 5,242,828 A | 9/1993 | Bergström et al. | |
| 5,252,459 A | 10/1993 | Tarcha et al. | |
| 5,262,299 A | 11/1993 | Evangelista et al. | |
| 5,268,306 A | 12/1993 | Berger et al. | |
| 5,275,785 A | 1/1994 | May et al. | |
| 5,314,923 A | 5/1994 | Cooke et al. | |
| 5,316,727 A | 5/1994 | Suzuki et al. | |
| 5,320,944 A | 6/1994 | Okada et al. | |
| 5,321,492 A | 6/1994 | Detwiler et al. | |
| 5,327,225 A | 7/1994 | Bender et al. | |
| 5,330,898 A | 7/1994 | Bar-Or et al. | |
| 5,342,759 A | 8/1994 | Litman et al. | |
| 5,352,582 A | 10/1994 | Lichtenwalter et al. | |
| 5,356,782 A | 10/1994 | Moorman et al. | |
| 5,358,852 A | 10/1994 | Wu | |
| 5,369,717 A | 11/1994 | Attridge | |
| 5,374,531 A | 12/1994 | Jensen | |
| 5,374,563 A | 12/1994 | Maule | |
| 5,376,255 A | 12/1994 | Gumbrecht et al. | |
| 5,387,503 A | 2/1995 | Selmer et al. | |
| 5,395,754 A | 3/1995 | Lambotte et al. | |
| 5,415,842 A | 5/1995 | Maule | |
| 5,418,136 A | 5/1995 | Miller et al. | |
| 5,424,219 A | 6/1995 | Jirikowski | |
| 5,424,841 A | 6/1995 | Van Gelder et al. | |
| 5,428,690 A | 6/1995 | Bacus et al. | |
| 5,432,057 A | 7/1995 | Litman et al. | |
| 5,436,161 A | 7/1995 | Bergström et al. | |
| 5,445,971 A | 8/1995 | Rohr | |
| 5,451,683 A | 9/1995 | Barrett et al. | |
| 5,455,475 A | 10/1995 | Josse et al. | |
| 5,464,741 A | 11/1995 | Hendrix | |
| 5,466,574 A | 11/1995 | Liberti et al. | |
| 5,467,778 A | 11/1995 | Catt et al. | |
| 5,468,606 A | 11/1995 | Bogart et al. | |
| 5,482,830 A | 1/1996 | Bogart et al. | |
| 5,482,867 A | 1/1996 | Barrett et al. | |
| 5,484,867 A | 1/1996 | Lichtenham et al. | |
| 5,489,678 A | 2/1996 | Fodor et al. | |
| 5,489,988 A | 2/1996 | Ackley et al. | |
| 5,492,840 A | 2/1996 | Malmqvist et al. | |
| 5,500,350 A | 3/1996 | Baker et al. | |
| 5,504,013 A | 4/1996 | Senior | |
| 5,508,171 A | 4/1996 | Walling et al. | |
| 5,510,481 A | 4/1996 | Bednarski et al. | |
| 5,512,131 A | 4/1996 | Kumar et al. | |
| 5,514,559 A | 5/1996 | Markert-Hahn et al. | |
| 5,514,785 A | 5/1996 | Van Ness et al. | |
| 5,516,635 A | 5/1996 | Ekins et al. | |
| 5,518,689 A | 5/1996 | Dosmann et al. | |
| 5,518,883 A | 5/1996 | Soini | |
| 5,527,711 A | 6/1996 | Tom-Moy et al. | |
| 5,534,132 A | 7/1996 | Vreeke et al. | |
| 5,554,539 A | 9/1996 | Chadney et al. | |
| 5,554,541 A | 9/1996 | Malmqvist et al. | |
| 5,569,608 A | 10/1996 | Sommer | |
| 5,571,684 A | 11/1996 | Lawrence et al. | |

| | | | |
|---|---|---|---|
| 5,573,909 A | 11/1996 | Singer et al. | |
| 5,573,919 A | 11/1996 | Kearns et al. | |
| 5,573,921 A * | 11/1996 | Behnke et al. ............... 436/514 | |
| 5,585,279 A | 12/1996 | Davidson | |
| 5,589,401 A | 12/1996 | Hansen et al. | |
| 5,591,581 A | 1/1997 | Massey et al. | |
| 5,591,645 A | 1/1997 | Rosenstein | |
| 5,596,414 A | 1/1997 | Tyler | |
| 5,599,668 A | 2/1997 | Stimpson et al. | |
| 5,602,040 A | 2/1997 | May et al. | |
| 5,610,077 A | 3/1997 | Davis et al. | |
| 5,618,732 A | 4/1997 | Pease et al. | |
| 5,618,888 A | 4/1997 | Choi et al. | |
| 5,620,850 A | 4/1997 | Bamdad et al. | |
| 5,622,871 A | 4/1997 | May et al. | |
| 5,637,509 A | 6/1997 | Hemmilä et al. | |
| 5,647,994 A | 7/1997 | Tuunanen et al. | |
| 5,656,503 A | 8/1997 | May et al. | |
| 5,658,443 A | 8/1997 | Yamamoto et al. | |
| 5,663,213 A | 9/1997 | Jones et al. | |
| 5,670,381 A | 9/1997 | Jou et al. | |
| 5,672,256 A | 9/1997 | Yee | |
| 5,700,636 A | 12/1997 | Sheiness et al. | |
| 5,714,389 A | 2/1998 | Charlton et al. | |
| 5,723,294 A | 3/1998 | Glass et al. | |
| 5,726,064 A | 3/1998 | Robinson et al. | |
| 5,731,147 A | 3/1998 | Bard et al. | |
| 5,736,188 A | 4/1998 | Alcock et al. | |
| 5,753,517 A | 5/1998 | Brooks et al. | |
| 5,770,416 A | 6/1998 | Lihme et al. | |
| 5,780,308 A | 7/1998 | Ching et al. | |
| 5,788,863 A | 8/1998 | Milunic | |
| 5,795,470 A | 8/1998 | Wang et al. | |
| 5,795,543 A | 8/1998 | Poto et al. | |
| 5,798,273 A | 8/1998 | Shuler et al. | |
| 5,811,526 A | 9/1998 | Davidson | |
| 5,827,748 A | 10/1998 | Golden | |
| 5,834,226 A | 11/1998 | Maupin | |
| 5,837,429 A | 11/1998 | Nohr et al. | |
| 5,837,546 A | 11/1998 | Allen et al. | |
| 5,837,547 A | 11/1998 | Schwartz | |
| 5,843,692 A | 12/1998 | Phillips et al. | |
| 5,852,229 A | 12/1998 | Josse et al. | |
| 5,876,944 A | 3/1999 | Kuo | |
| 5,885,527 A | 3/1999 | Buechler | |
| 5,906,921 A | 5/1999 | Ikeda et al. | |
| 5,910,286 A | 6/1999 | Lipskie | |
| 5,910,447 A | 6/1999 | Lawrence et al. | |
| 5,910,940 A | 6/1999 | Guerra | |
| 5,922,537 A | 7/1999 | Ewart et al. | |
| 5,922,550 A | 7/1999 | Everhart et al. | |
| 5,943,129 A | 8/1999 | Hoyt et al. | |
| 5,945,281 A | 8/1999 | Prabhu | |
| 5,951,492 A | 9/1999 | Douglas et al. | |
| 5,962,995 A | 10/1999 | Avnery | |
| 5,968,839 A | 10/1999 | Blatt et al. | |
| 5,985,432 A | 11/1999 | Wang et al. | |
| 5,989,924 A | 11/1999 | Root et al. | |
| 5,989,926 A | 11/1999 | Badley et al. | |
| 5,998,221 A | 12/1999 | Malick et al. | |
| 6,004,530 A | 12/1999 | Sagner et al. | |
| 6,008,892 A | 12/1999 | Kain et al. | |
| 6,020,047 A | 2/2000 | Everhart | |
| 6,027,904 A | 2/2000 | Devine et al. | |
| 6,027,944 A | 2/2000 | Robinson et al. | |
| 6,030,792 A | 2/2000 | Otterness et al. | |
| 6,030,840 A | 2/2000 | Mullinax et al. | |
| 6,033,574 A | 3/2000 | Siddiqi | |
| 6,048,623 A | 4/2000 | Everhart et al. | |
| 6,057,165 A | 5/2000 | Mansour | |
| 6,060,256 A | 5/2000 | Everhart et al. | |
| 6,077,669 A | 6/2000 | Little et al. | |
| 6,080,391 A | 6/2000 | Tsuchiya et al. | |
| 6,084,683 A | 7/2000 | Bruno et al. | |
| 6,087,184 A | 7/2000 | Magginetti et al. | |
| 6,099,484 A | 8/2000 | Douglas et al. | |
| 6,103,537 A | 8/2000 | Ullman et al. | |
| 6,117,090 A | 9/2000 | Caillouette | |
| 6,130,100 A | 10/2000 | Jobling et al. | |
| 6,133,048 A | 10/2000 | Penfold et al. | |
| 6,136,549 A | 10/2000 | Feistel | |
| 6,136,611 A | 10/2000 | Saaski et al. | |
| 6,139,961 A | 10/2000 | Blankenship et al. | |
| 6,151,110 A | 11/2000 | Markart | |
| 6,156,271 A | 12/2000 | May | |
| 6,165,798 A | 12/2000 | Brooks | |
| 6,171,780 B1 | 1/2001 | Pham et al. | |
| 6,171,870 B1 | 1/2001 | Freitag | |
| 6,174,646 B1 | 1/2001 | Hirai et al. | |
| 6,177,281 B1 | 1/2001 | Manita | |
| 6,180,288 B1 | 1/2001 | Everhart et al. | |
| 6,183,972 B1 | 2/2001 | Kuo et al. | |
| 6,184,042 B1 | 2/2001 | Neumann et al. | |
| 6,187,269 B1 | 2/2001 | Lancesseru et al. | |
| 6,194,220 B1 | 2/2001 | Malick et al. | |
| 6,200,820 B1 | 3/2001 | Hansen et al. | |
| 6,221,238 B1 | 4/2001 | Grundig et al. | |
| 6,221,579 B1 | 4/2001 | Everhart et al. | |
| 6,234,974 B1 | 5/2001 | Catt et al. | |
| 6,235,241 B1 | 5/2001 | Catt et al. | |
| 6,235,471 B1 | 5/2001 | Knapp et al. | |
| 6,235,491 B1 | 5/2001 | Connolly | |
| 6,241,863 B1 | 6/2001 | Monbouquette | |
| 6,242,268 B1 | 6/2001 | Wieder et al. | |
| 6,255,066 B1 | 7/2001 | Louderback | |
| 6,261,779 B1 | 7/2001 | Barbera-Guillem et al. | |
| 6,268,222 B1 | 7/2001 | Chandler et al. | |
| 6,270,637 B1 | 8/2001 | Crismore et al. | |
| 6,271,040 B1 | 8/2001 | Buechler | |
| 6,274,324 B1 | 8/2001 | Davis et al. | |
| 6,281,006 B1 | 8/2001 | Heller et al. | |
| 6,284,472 B1 | 9/2001 | Wei et al. | |
| 6,287,783 B1 | 9/2001 | Maynard et al. | |
| 6,287,871 B1 | 9/2001 | Herron et al. | |
| 6,294,391 B1 | 9/2001 | Badley et al. | |
| 6,294,392 B1 | 9/2001 | Kuhr et al. | |
| 6,306,665 B1 | 10/2001 | Buck et al. | |
| D450,854 S | 11/2001 | Lipman et al. | |
| 6,331,438 B1 | 12/2001 | Aylott et al. | |
| 6,348,186 B1 | 2/2002 | Sutton et al. | |
| 6,352,862 B1 | 3/2002 | Davis et al. | |
| 6,362,011 B1 | 3/2002 | Massey et al. | |
| 6,368,873 B1 | 4/2002 | Chang et al. | |
| 6,368,875 B1 | 4/2002 | Geisberg | |
| 6,387,707 B1 | 5/2002 | Seul et al. | |
| 6,391,558 B1 | 5/2002 | Henkens et al. | |
| 6,396,053 B1 | 5/2002 | Yokoi | |
| 6,399,295 B1 | 6/2002 | Kaylor et al. | |
| 6,399,397 B1 | 6/2002 | Zarling et al. | |
| 6,399,398 B1 | 6/2002 | Cunningham et al. | |
| 6,407,492 B1 | 6/2002 | Avnery et al. | |
| 6,411,439 B2 | 6/2002 | Nishikawa | |
| 6,413,410 B1 | 7/2002 | Hodges et al. | |
| 6,436,651 B1 | 8/2002 | Everhart et al. | |
| 6,436,722 B1 | 8/2002 | Clark et al. | |
| 6,444,423 B1 | 9/2002 | Meade et al. | |
| 6,448,091 B1 | 9/2002 | Massey et al. | |
| 6,451,607 B1 | 9/2002 | Lawrence et al. | |
| 6,455,861 B1 | 9/2002 | Hoyt | |
| 6,461,496 B1 | 10/2002 | Feldman et al. | |
| 6,468,741 B1 | 10/2002 | Massey et al. | |
| 6,472,226 B1 | 10/2002 | Barradine et al. | |
| 6,473,239 B1 | 10/2002 | Völcker et al. | |
| 6,479,146 B1 | 11/2002 | Caruso et al. | |
| 6,483,582 B2 | 11/2002 | Modlin et al. | |
| 6,509,085 B1 | 1/2003 | Kennedy | |
| 6,509,196 B1 | 1/2003 | Brooks et al. | |
| 6,511,814 B1 | 1/2003 | Carpenter | |
| 6,524,864 B2 | 2/2003 | de Castro | |
| 6,556,299 B1 | 4/2003 | Rushbrooke et al. | |
| 6,566,508 B2 | 5/2003 | Bentsen et al. | |
| 6,573,040 B2 | 6/2003 | Everhart et al. | |
| 6,579,673 B2 | 6/2003 | McGrath et al. | |
| 6,582,930 B1 | 6/2003 | Ponomarev et al. | |
| 6,585,939 B1 | 7/2003 | Dapprich | |
| 6,607,922 B2 | 8/2003 | LaBorde | |
| 6,613,583 B1 | 9/2003 | Richter et al. | |
| 6,617,488 B1 | 9/2003 | Springer et al. | |

| | | | |
|---|---|---|---|
| 6,627,459 B1 | 9/2003 | Tung et al. | |
| 6,653,149 B1 | 11/2003 | Tung et al. | |
| 6,665,072 B2 | 12/2003 | Hoyt | |
| 6,669,908 B2 | 12/2003 | Weyker et al. | |
| 6,670,115 B1 | 12/2003 | Zhang | |
| RE38,430 E | 2/2004 | Rosenstein | |
| 6,699,722 B2 * | 3/2004 | Bauer et al. | 436/518 |
| 6,720,007 B2 | 4/2004 | Walt et al. | |
| 6,750,031 B1 * | 6/2004 | Ligler et al. | 435/7.93 |
| 6,787,368 B1 | 9/2004 | Wong et al. | |
| 6,815,218 B1 | 11/2004 | Jacobson et al. | |
| 6,916,666 B1 | 7/2005 | Mendel-Hartvig et al. | |
| 6,951,631 B1 | 10/2005 | Catt et al. | |
| 7,044,919 B1 | 5/2006 | Catt et al. | |
| 7,052,831 B2 | 5/2006 | Fletcher et al. | |
| 7,144,742 B2 * | 12/2006 | Boehringer et al. | 436/514 |
| 2001/0055776 A1 | 12/2001 | Greenwalt | |
| 2002/0042149 A1 | 4/2002 | Butlin et al. | |
| 2002/0045273 A1 | 4/2002 | Butlin et al. | |
| 2002/0052048 A1 | 5/2002 | Stein et al. | |
| 2002/0070128 A1 | 6/2002 | Beckmann | |
| 2002/0132282 A1 | 9/2002 | Ouyang et al. | |
| 2002/0146754 A1 | 10/2002 | Kitawaki et al. | |
| 2002/0146844 A1 * | 10/2002 | Pronovost et al. | 436/514 |
| 2002/0167662 A1 | 11/2002 | Tanaami et al. | |
| 2002/0177235 A1 | 11/2002 | Mabile et al. | |
| 2003/0017615 A1 | 1/2003 | Sidwell et al. | |
| 2003/0119202 A1 | 6/2003 | Kaylor et al. | |
| 2003/0119204 A1 | 6/2003 | Wei et al. | |
| 2003/0124739 A1 | 7/2003 | Song et al. | |
| 2003/0157727 A1 | 8/2003 | Nagano et al. | |
| 2003/0162236 A1 | 8/2003 | Harris et al. | |
| 2003/0175517 A1 | 9/2003 | Voigt et al. | |
| 2003/0178309 A1 | 9/2003 | Huang et al. | |
| 2004/0014073 A1 | 1/2004 | Trau et al. | |
| 2004/0018637 A1 * | 1/2004 | Polito et al. | 436/514 |
| 2004/0043502 A1 | 3/2004 | Song et al. | |
| 2004/0043507 A1 | 3/2004 | Song et al. | |
| 2004/0043511 A1 | 3/2004 | Song et al. | |
| 2004/0043512 A1 | 3/2004 | Song et al. | |
| 2004/0106190 A1 | 6/2004 | Yang et al. | |
| 2004/0130715 A1 | 7/2004 | Dosaka et al. | |
| 2004/0151632 A1 | 8/2004 | Badley et al. | |
| 2004/0152963 A1 | 8/2004 | March | |
| 2005/0170527 A1 * | 8/2005 | Boehringer et al. | 436/514 |
| 2005/0196875 A1 * | 9/2005 | Blatt et al. | 436/514 |
| 2006/0029924 A1 | 2/2006 | Brewster et al. | |

FOREIGN PATENT DOCUMENTS

| | | |
|---|---|---|
| EP | 0205698 A1 | 12/1986 |
| EP | 0420053 A1 | 4/1991 |
| EP | 0437287 B1 | 7/1991 |
| EP | 0703454 A1 | 3/1996 |
| EP | 0462376 B1 | 7/1996 |
| EP | 0724156 A1 | 7/1996 |
| EP | 0745843 A2 | 12/1996 |
| EP | 0745843 A3 | 12/1996 |
| EP | 0859230 A1 | 8/1998 |
| EP | 0898169 B1 | 2/1999 |
| EP | 1221616 A1 | 7/2002 |
| GB | 2273772 A | 6/1994 |
| WO | WO 8804777 A1 | 6/1988 |
| WO | WO 9105999 A2 | 5/1991 |
| WO | WO 9221769 A1 | 12/1992 |
| WO | WO 9221770 A1 | 12/1992 |
| WO | WO 9221975 A1 | 12/1992 |
| WO | WO 9301308 A1 | 1/1993 |
| WO | WO 9319370 A1 | 9/1993 |
| WO | WO 9413835 A1 | 6/1994 |
| WO | WO 9415193 A1 | 7/1994 |
| WO | WO 9709620 A1 | 3/1997 |
| WO | WO 9910742 A1 | 3/1999 |
| WO | WO 9930131 A1 | 6/1999 |
| WO | WO 9936777 A1 | 7/1999 |
| WO | WO 9964864 A1 | 12/1999 |
| WO | WO 0019199 A1 | 4/2000 |
| WO | WO 0023805 A1 | 4/2000 |
| WO | WO 0046839 A2 | 8/2000 |
| WO | WO 0046839 A3 | 8/2000 |
| WO | WO 0047983 A1 | 8/2000 |
| WO | WO 0050891 A1 | 8/2000 |
| WO | WO 0078917 A1 | 12/2000 |
| WO | WO 0138873 A2 | 5/2001 |
| WO | WO 0163299 A1 | 8/2001 |
| WO | WO 0198765 A1 | 12/2001 |
| WO | WO 0198785 A2 | 12/2001 |
| WO | WO 02097408 A1 | 12/2002 |
| WO | WO 03005013 A1 | 1/2003 |
| WO | WO 2004034056 A2 | 4/2004 |
| WO | WO 2004034056 A3 | 4/2004 |

OTHER PUBLICATIONS

U.S. Appl. No. 10/406,577, filed Apr. 3, 2003, Yang, et al., Assay Devices That Utilize Hollow Particles.

U.S. Appl. No. 10/325,614, filed Dec. 19, 2002, Wei et al., Reduction Of The Hook Effect In Membrane-Based Assay Devices.

U.S. Appl. No. 10/406,631, filed Apr. 3, 2003, Wei et al., Reduction Of The Hook Effect In Assay Devices.

U.S. Appl. No. 10/719,976, filed Nov. 21, 2003, Xuedong Song, Method for Extending The Dynamic Detection Range Of Assay Devices.

U.S. Appl. No. 10/741,434, filed Dec. 19, 2003, Yang, et al., Laminated Assay Devices.

U.S. Appl. No. 10/742,589, filed Dec. 19, 2003, Yang, et al., Flow Control Of Electrochemical-Based Assay Devices.

U.S. Appl. No. 10/742,590, filed Dec. 19, 2003, Yang, et al., Flow-Through Assay Devices.

U.S. Appl. No. 10/718,989, filed Nov. 21, 2003, Xuedong Song, Membrane-Based Lateral Flow Assay Devices That Utilize Phosphorescent Detection.

U.S. Appl. No. 10/718,996, filed Nov. 21, 2003, Ning Wei, Method Of Reducing The Sensitivity Of Assay Devices.

U.S. Appl. No. 10/836,093, filed Apr. 30, 2004, David S. Cohen, Optical Detection Systems.

U.S. Appl. No. 10/790,617, filed Mar. 1, 2004, Boga, et al., Assay Devices Utilizing Chemichronic Dyes.

Abstract of Japanese Patent No. JP 8062214, Mar. 8, 1996.

Abstract of Article—*Factors influencing the formation of hollow ceramic microspheres by water extraction of colloidal droplets*, J. Mater. Res., vol. 10, No. 1, p. 84.

Article—*A conductometric biosensor for biosecurity*, Zarini Muhammid-Tahir and Evangelyn C. Alocilja, Biosensors and Bioelectronics 18, 2003, pp. 813-819.

Article—*A Disposable Amperometric Sensor Screen Printed on a Nitrocellulose Strip: A Glucose Biosensor Employing Lead Oxide as an Interference-Removing Agent*, Gang Cui, San Jin Kim, Sung Hyuk Choi, Hakhyun Nam, and Geun Sig Cha, Analytical Chemistry, vol. 72, No. 8, Apr. 15, 2000, pp. 1925-1929.

Article—*A Fully Active Monolayer Enzyme Electrode Derivatized by Antigen-Antibody Attachment*, Christian Bourdillon, Christopher Demaille, Jean Gueris, Jacques Moiroux, and Jean-Michel Savéant, J. Am. Chem. Soc., vol. 115, No. 26, 1993, pp. 12264-12269.

Article—*A New Tetradentate β-Diketonate-Europium Chelate That Can Be Covalently Bound to Proteins for Time-Resolved Fluoroimmunoassay*, Jingli Yuan and Kazuko Matsumoto, Analytical Chemistry, vol. 70, No. 3, Feb. 1, 1998, pp. 596-601.

Article—*A Thermostable Hydrogen Peroxide Sensor Based on "Wiring" of Soybean Peroxidase*, Mark S. Vreeke, Khin Tsun Yong, and Adam Heller, Analytical Chemistry, vol. 67, No. 23, Dec. 1, 1995, pp. 4247-4249.

Article—*Acoustic Plate Waves for Measurements of Electrical Properties of Liquids*, U. R. Kelkar, F. Josse, D. T. Haworth, and Z. A. Shana, Micromechanical Journal, vol. 43, 1991, pp. 155-164.

Article—*Amine Content of Vaginal Fluid from Untreated and Treated Patients with Nonspecific Vaginitis*, Kirk C.S. Chen, Patricia S. Forsyth, Thomas M. Buchanan, and King K. Holmes, J. Clin. Invest., vol. 63, May 1979, pp. 828-835.

Article—*Analysis of electrical equivalent circuit of quartz crystal resonator loaded with viscous conductive liquids*, Journal of Electroanalytical Chemistry, vol. 379, 1994, pp. 21-33.

Article—*Application of rod-like polymers with ionophores as Langmuir-Blodgett membranes for Si-based ion sensors*, Sensors and Actuators B, 1992, pp. 211-216.

Article—*Attempts to Mimic Docking Processes of the Immune System: Recognition of Protein Multilayers*, W. Müller, H. Ringsdorf, E. Rump, G. Wildburg, X. Zhang, L. Angermaier, W. Knoll, M. Liley, and J. Spinke, Science, vol. 262, Dec. 10, 1993, pp. 1706-1708.

Article—*Biochemical Diagnosis of Vaginitis: Determination of Diamines in Vaginal Fluid*, Kirk C.S. Chen, Richard Amsel, David A. Eschenbach, and King K. Holmes, The Journal of Infectious Diseases, vol. 145, No. 3, Mar. 1982, pp. 337-345.

Article—*Biospecific Adsorption of Carbonic Anhydrase to Self-Assembled Monolayers of Alkanethiolates That Present Benzenesulfonamide Groups on Gold*, Milan Mrksich, Jocelyn R. Grunwell, and George M. Whitesides, J. Am. Chem. Soc., vol. 117, No. 48, 1995, pp. 12009-12010.

Article—*Direct Observation of Streptavidin Specifically Adsorbed on Biotin-Functionalized Self-Assembled Monolayers with the Scanning Tunneling Microscope*, Lukas Häussling, Bruno Michel, Helmut Ringsdorf, and Heinrich Rohrer, Angew Chem. Int. Ed. Engl., vol. 30, No. 5, 1991, pp. 569-572.

Article—*Electrical Surface Perturbation of a Piezoelectric Acoustic Plate Mode by a Conductive Liquid Loading*, Fabien Josse, IEEE Transactions on Ultrasonics, Ferroelectrics, and Frequency Control, vol. 39, No. 4, Jul. 1992, pp. 512-518.

Article—*Europium Chelate Labels in Time-Resolved Fluorescence Immunoassays and DNA Hybridization Assays*, Eleftherios P. Diamandis and Theodore K. Christopoulos, Analytical Chemistry, vol. 62, No. 22, Nov. 15, 1990, pp. 1149-1157.

Article—*Evaluation of a Time-Resolved Fluorescence Microscope Using a Phosphorescent Pt-Porphine Model System*, E. J. Hennink, R. de Haas, N. P. Verwoerd, and H. J. Tanke, Cytometry, vol. 24, 1996, pp. 312-320.

Article—*Fabrication of Patterned, Electrically Conducting Polypyrrole Using a Self-Assembled Monolayer: A Route to All-Organic Circuits*, Christopher B. Gorman, Hans A. Biebuyck, and George M. Whitesides, American Chemical Society, 2 pages.

Article—*Fabrication of Surfaces Resistant to Protein Adsorption and Application to Two-Dimensional Protein Patterning*, Suresh K. Bhatia, John L. Teixeira, Mariquita Anderson, Lisa C. Shriver-Lake, Jeffrey M. Calvert, Jacque H. Georger, James J. Hickman, Charles S. Dulcey, Paul E. Schoen, and Frances S. Ligler, Analytical Biochemistry, vol. 208, 1993, pp. 197-205.

Article—*Features of gold having micrometer to centimeter dimensions can be formed through a combination of stamping with an elastomeric stamp and an alkanethiol "ink" followed by chemical etching*, Amit Kumar and George M. Whitesides, Appl. Phys. Lett., vol. 63, No. 14, Oct. 4, 1993, pp. 2002-2004.

Article—*Fine Structure of Human Immunodeficiency Virus (HIV) and Immunolocalization of Structural Proteins*, Hans R. Gelderblom, Elda H.S. Hausmann, Muhsin Özel, George Pauli, and Meinrad A. Koch, Virology, vol. 156, No. 1, Jan. 1987, pp. 171-176.

Article—Flow-*Based Microimmunoassay*. Analytical Chemistry, vol. 73, No. 24, Mark A. Hayes, Nolan A. Poison, Allison, N. Phayre, and Antonia A. Garcia, Dec. 15, 2001, pp. 5896-5902.

Article—*Generation of electrochemically deposited metal patterns by means of electron beam (nano)lithography of self-assembled monolayer resists*, J. A. M. Sondag-Hethorst, H. R. J. van-Helleputte, and L. G. J. Fokkink, Appl. Phys. Lett., vol. 64, No. 3, Jan. 17, 1994, pp. 285-287.

Article—*Heterogeneous Enzyme Immunoassay of Alpha-Fetoprotein in Maternal Senun by Flow-Injection Amperometric Detection of 4-Aminophenol*, Yan Xu, H. Brian Haisall, and William R. Heineman, Clinical Chemistry, vol. 36, No. 11, 1990, pp. 1941-1944.

Article—*Hollow latex particles: synthesis and applications*, Charles J. McDonald and Michael J. Devon, Advances in Colloid and Interface Science, Vo. 99, 2002, pp. 181-213.

Article—*How to Build a Spectrofluorometer*, Spex Fluorolog 3, Horiba Group, pp. 1-14.

Article—*Hydrogen Peroxide and β-Nicotinamide Adenine Dinucleotide Sensing Amperometric Electrodes Based on Electrical Connection of Horseradish Peroxidase Redox Centers to Electrodes Through a Three-Dimensional Electron Relaying Polymer Network*, Mark Vreeke, Ruben Maidan, and Adam Heller, Analytical Chemistry, vol. 64, No. 24, Dec. 15, 1992, pp. 3084-3090.

Article—*Immunoaffinity Based Phosphorescent Sensor Platform for the Detection of Bacterial Spores*, Peter F. Scholl, C. Brent Bargeron, Terry E. Phillips, Tommy Wong, Sala Abubaker, John D. Groopman, Paul T. Strickland, and Richard C. Benson, Proceedings of SPIE, vol. 3913, 2000, pp. 204-214.

Article—*Inert Phosphorescent Nanospheres as Markers for Optical Assays*, Jens M. Kürner, Ingo Klimant, Christian Krause, Harald Preu, Werner Kunz, and Otto S. Wolfbeis, Bioconjugate Chem., vol. 12, No. 6, 2001, pp. 883-889.

Article—*Intelligent Gels*, Yoshihito Osada and Simon B. Ross-Murphy, Scientific American, May 1993, pp. 82-87.

Article—*Latex Immunoassays*, Leigh B. Bangs, Journal of Clinical Immunoassay, vol. 13, No. 3, 1990, pp. 127-131.

Article—*Longwave luminescent porphyrin probes*, Dmitry B. Papkovsky, Gelii P. Ponomarev, and Otto S. Wolibeis, Spectrochimica Acta Part A 52, 1996, pp. 1629-1638.

Article—*Mechanical resonance gas sensors with piezoelectric excitation and detection using PVDF polymer foils*, R. Block, G. Fickler, G. Lindner, H. Müller, and M. Wohnhas, Sensors and Actuators B, 1992, pp. 596-601.

Article—*Microfabrication by Microcontact Printing Of Self-Assembled Monolyaers*, James L. Wilbur, Armit Kumar, Enoch Kim, and George M. Whitesides, Advanced Materials, vol. 6, No. 7/8, 1994, pp. 600-604.

Article—*Modification of monoclonal and polyclonal IgG with palladium (II) coproporphyrin I: stimulatory and inhibitory functional effects induced by two different methods*, Sergey P. Martsev, Valery A. Preygerzon, Yanina I. Mel'nikova, Zinaida I. Kravehulk, Gely V. Ponomarev, Vitaly E. Lunev, and Alexander P. Savitsky, Journal of Immunological Methods 186, 1996, pp. 293-304.

Article—*Molecular Design Temperature-Responsive Polymers as Intelligent Materials*, Teruo Okano, Advances in Polymer Science, pp. 179-197.

Article—*Molecular Gradients of w-Substituted Alkanethiols on Gold: Preparation and Characterization*, Bo Liedberg and Pentti Tengvall, Langmuir, vol. 11, No. 10, 1995, pp. 3821-3827.

Article—*Monofunctional Dervatives of Coproporphyrins for Phosphorescent Labeling of Proteins and Binding Assays*, Tomás C. O'Riordan, Aleksi E. Soini, and Dmitri B. Papkovsky, Analytical Biochemistry, vol. 290, 2001, pp. 366-375.

Article—*Nanostructured™ Chemicals: Bridging the Gap Between Fillers, Surface Modifications and Reinforcement*, Joseph D. Lichtenhan, Invited lectures: Functional Tire Fillers 2001, Ft. Lauderdale, FL, Jan. 29-31, 2001, pp. 1-15.

Article—*Near Infrared Phosphorescent Metalloporphrins*, Alexander P. Savitsky Anna V. Savitskaja, Eugeny A. Lukjanetz, Svetlana N. Dashkevich, and Elena A. Makarova, SPIE, vol. 2980, pp. 352-357.

Article—*New Approach to Producing Patterned Biomolecular Assemblies*, Suresh K. Bhatia, James J. Hickman, and Frances S. Ligler, J. Am. Chem. Soc., vol. 114, 1992, pp. 4433-4434.

Article—*On the use of ZX-LiNbO$_3$ acoustic plate mode devices as detectors for dilute electrolytes*, F. Josse, Z. A. Shana, D. T. Haworth, and S. Liew, Sensors and Actuators B, vol. 9, 1992, pp. 92-112.

Article—*One-step all-in-one dry reagent immunoassays with fluorescent europium chelate label and time-resolved fluorometry*, Timo Lövgren, Liisa Meriö, Katja Mitrunen, Maija-Liisa Mäkinen, Minna Mäkelä, Kaj Blomberg, Tom Palenius, and Kim Pettersson, Clinical Chemistry 42:8, 1996, pp. 1196-1201.

Article—*Optical Biosensor Assay (OBA™)*, Y. G. Tsay, C. I. Lin, J. Lee, E. K. Gustafson, R. Appelqvist, P. Magginetti, R. Norton, N. Teng, and D. Charlton, Clinical Chemistry, vol. 37, No. 9, 1991, pp. 1502-1505.

Article—*Order in Microcontact Printed Self-Assembled Monolayers*, N. B. Larsen, H. Biebuyck, E. Delamarche, and B. Michel, J. Am. Chem. Soc., vol. 119, No. 13, 1997, pp. 3017-3026.

Article—*Orientation dependence of surface segregation in a dilute Ni-Au alloy*, W. C. Johnson, N. G. Chavka, R. Ku, J. L. Bomback, and P. P. Wynblatt, J. Vac. Sci. Technol. vol. 15, No. 2, Mar./Apr. 1978, pp. 467-469.

Article—*Patterned Condensation Figures as Optical Diffraction Gratings*, Amit Kumar and George M. Whitesides, Science, vol. 263, Jan. 7, 1994, pp. 60-62.

Article—*Patterned Functionalization of Gold and Single Crystal Silicon via Photochemical Reaction of Surface-Confined Derivatives of ($n^5$-$C_5H_5$)$Mn(CO)_3$*, Doris Kang and Mark S. Wrigthton, Langmuir, vol. 7, No. 10, 1991, pp. 2169-2174.

Article—*Patterned Metal Electrodeposition Using an Alkanethiolate Mask*, T. P. Moffat H. Yang, J. Electrochem. Soc., vol. 142, No. 11, Nov. 1995, pp. L220-L222.

Article—*Performance Evaluation of the Phosphorescent Porphyrin Label: Solid-Phase Immunoassay of α-Fetoprotein*, Tomás C. O'Riordan, Aleksi E. Soini, Juhani T. Soini, and Dmitri B. Papkovsky, Analytical Chemistry, vol. 74, No. 22, Nov. 15, 2002, pp. 5845-5850.

Article—*Phosphorescent porphyrin probes in biosensors and sensitive bioassays*, D. B. Papkovsky, T. O'Riordan, and A. Soini, Biochemical Society Transactions, vol. 28, part 2, 2000, pp. 74-77.

Article—*Photolithography of self-assembled monolayers: optimization of protecting groups by an electroanalytical method*, Jamila Jennane, Tanya Boutrous, and Richard Giasson, Can. J. Chem., vol. 74, 1996, pp. 2509-2517.

Article—*Photopatterning and Selective Electroless Metallization of Surface-Attached Ligands*, Walter J. Dressick, Charles S. Dulcey, Jacque H. Georger, Jr., and Jeffrey M. Calvert, American Chemical Society, 2 pages.

Article—*Photosensitive Self-Assembled Monolayers on Gold: Photochemistry of Surface-Confined Aryl Azide and Cyclopentadienylmanganese Tricarbonyl*, Eric W. Wollman, Doris Kang, C. Daniel Frisbie, Ivan M. Lorkovic and Mark S. Wrighton, J. Am. Chem. Soc., vol. 116, No. 10, 1994, pp. 4395-4404.

Article—*Polymer Based Lanthanide Luminescent Sensors for the Detection of Nerve Agents*, Amanda L. Jenkins, O. Manuel Uy, and George M. Murray, Analytical Communications, vol. 34, Aug. 1997, pp. 221-224.

Article—*Prediction of Segregation to Alloy Surfaces from Bulk Phase Diagrams*, J. J. Burton and E. S. Machlin, Physical Review Letters, vol. 37, No. 21, Nov. 22, 1976, pp. 1433-1436.

Article—*Principle and Applications of Size-Exclusion Chromatography*, Impact Analytical, pp. 1-3.

Article—*Probing of strong and weak electrolytes with acoustic wave fields*, R. Dahint, D. Grunze, F. Josse, and J. C. Andle, Sensors and Actuators B, vol. 9, 1992, pp. 155-162.

Article—*Production of Hollow Microspheres from Nanostructured Composite Particles*, Frank Caruso, Rachel A. Caruso, and Helmuth MöhwaldChem, Mater., vol. 11, No. 11, 1999, pp. 3309-3314.

Article—*Quantitative Prediction of Surface Segregation*, M. P. Seah, Journal of Catalysts, vol. 57, 1979, pp. 450-457.

Article—*Quartz Crystal Resonators as Sensors in Liquids Using the Acoustoelectric Effect*, Zack A. Shana and Fabian Josse, Analytical Chemistry, vol. 66, No. 13, Jul. 1, 1994, pp. 1955-1964.

Article—*Responsive Gels: Volume Transitions I*, M. Ilaysky, H. Inomata, A. Khokhlove, M. Konno, A. Onuki, S. Saito, M. Shibayama, R.A. Siegel, S. Starodubtzev, T. Tanaka, and V. V. Vasiliveskaya, Advances in Polymer Science, vol. 109, 9 pages.

Article—*Room-Temperature Phosphorescent Palladium—Porphine Probe for DNA Determination*, Montserrat Roza-Fernández, Maria Jesús Valencia-González, and Marta Elena Diaz-Garcia, Analytical Chemistry, vol. 69, No. 13, Jul. 1, 1997, pp. 2406-2410.

Article—*Self-Assembled Monolayer Films for Nanofabrication*, Elizabeth A. Dobisz, F. Keith Perkins, Susan L. Brandow, Jeffrey M. Calvert, and Christie R. K. Marrian, Mat. Res. Soc. Symp. Proc., vol. 380, 1995, pp. 23-34.

Article—*Sensing liquid properties with thickness-shear mode resonators*, S. J. Martin, G. C. Frye, and K. O. Wessendorf, Sensors and Actuators A, vol. 44, 1994, pp. 209-218.

Article—*Separation-Free Sandwich Enzyme Immunoassays Using Microporous Gold Electrodes and Self-Assembled Monolayer/Immobilized Capture Antibodies*, Chuanming Duan and Mark E. Meyerhoff, Analytical Chemistry, vol. 66, No. 9, May 1, 1994, pp. 1369-1377.

Article—*Stimuli-Responsive Poly(N-isopropylacrylamide) Photo- and Chemical-Induced Phase Transitions*, Advances in Polymer Science, pp. 50-65.

Article—*The Adsorptive Characteristics of Proteins for Polystyrene and Their Significance in Solid-Phase Immunoassays*, L. A. Cantaero, J. E. Butler, and J. W. Osborne, Analytical Biochemistry, vol. 105, 1980, pp. 375-382.

Article—*The Use of Self-Assembled Monolayers and a Selective Etch to Generate Patterned Gold Features*, Amit Kumar, Hans A. Biebuyck, Nicholas L. Abbott, and George M. Whitesides, Journal of the American Chemical Society, vol. 114, 1992, 2 pages.

Article—*Volume Phase Transition of N-Alkylacrylamide Gels*, S. Saito, M. Konno, and H. Inomala, Advances in Polymer Science, vol. 109, 1992, pp. 207-232.

Article—*Whole Blood Capcellia CD4/CD8 Immunoassay for Enumeration of CD4+ and CD8+ Peripheral T Lymphocytes*, Dominique Carrière, Jean Pierre Vendrell, Claude Fontaine, Aline Jansen, Jacques Reynes, Isabelle Pagès, Catherine Holzmann, Michel Laprade, and Bernard Pau, Clinical Chemistry, vol. 45, No. 1, 1999, pp. 92-97.

8 Photographs of Accu-chek® Blood Glucose Meter.

*AMI Screen Printers*—Product Information, 4 pages.

*Dualite® Polymeric Microspheres*, from Pierce & Stevens Corp. a subsidiary of Sovereign Specialty Chemicals, Inc., 2 pages.

*Dynabeads® Biomagnetic Separation Technology—The Principle* from Dynal Biotech, 2 pages.

*Fluorescent Microsphere Standards for Flow Cytometry and Fluorescence Microscopy* from Molecular Probes, pp. 1-8.

*FluoSpheres® Fluorescent Microspheres*, Product Information from Molecular Probes, Mar. 13, 2001, pp. 1-6.

*Magnetic Microparticles*, Polysciences, Inc. Technical Data Sheet 438, 2 pages.

*Making sun exposure safer for everyone* from Rohm and Haas Company (Bristol Complex), 2 pages.

Pamphlet—The ClearPlan® Easy Fertility Monitor.

*POSS Polymer Systems* from Hybrid Plastics, 3 pages.

*The colloidal state*, Introduction to Colloid and Surface Chemistry, $4^{th}$ Ed., 17 pages.

*Working With FluoSpheres® Fluorescent Microspheres*, Properties and Modifications, Product Information from Molecular Probes, Mar. 9, 2001, pp. 1-5.

PCT Search Report for PCT/US03/21520, Dec. 15, 2003.
PCT Search Report for PCT/US02/37653, Apr. 7, 2004.
PCT Search Report for PCT/US03/28628, Mar. 18, 2004.
PCT Search Report for PCT/US03/34543, Apr. 6, 2004.
PCT Search Report for PCT/US03/34544, Aug. 17, 2004.
Abstract of DE10024145A1, Nov. 22, 2001.

Article—*Solid Substrate Phosphorescent Immunoassay Based On Bioconjugated Nanoparticles*, Baoquan Sun, Guangshun Yi, Shuying Zhao, Depu Chen, Yuxiang Zhou, and Jing Cheng, Analytical Letters, vol. 34, No. 10, 2001, pp. 1627-1637.

PCT Search Report and Written Opinion for PCT/US2004/013180.

Article—*New Use of Cyanosilane Coupling Agent for Direct Binding of Antibodies to Silica Supports. Physicochemical Characterization of Molecularly Bioengineered Layers*, Sandrine Falipou, Jean-Marc Chovelon, Claude Martelet, Jacqueline Margonari and Dominique Cathignol, Bioconjugate Chem., vol. 10, No. 3, 1999, pp. 346-353.

PCT Search Report and Written Opinion for PCT/US2004/006412, Sep. 28, 2004.

PCT Search Report and Written Opinion for PCT/US2004/006414, Sep. 28, 2004.

* cited by examiner

EXTENSION OF THE DYNAMIC DETECTION RANGE OF ASSAY DEVICES

BACKGROUND OF THE INVENTION

Various analytical procedures and devices are commonly employed in flow-through assays to determine the presence and/or concentration of analytes that may be present in a test sample. For instance, immunoassays utilize mechanisms of the immune systems, wherein antibodies are produced in response to the presence of antigens that are pathogenic or foreign to the organisms. These antibodies and antigens, i.e., immunoreactants, are capable of binding with one another, thereby causing a highly specific reaction mechanism that may be used to determine the presence or concentration of that particular antigen in a biological sample.

There are several well-known immunoassay methods that use immunoreactants labeled with a detectable component so that the analyte may be detected analytically. For example, "sandwich-type" assays typically involve mixing the test sample with detectable probes, such as dyed latex or a radioisotope, which are conjugated with a specific binding member for the analyte. The conjugated probes form complexes with the analyte. These complexes then reach a zone of immobilized antibodies where binding occurs between the antibodies and the analyte to form ternary "sandwich complexes." The sandwich complexes are localized at the zone for detection of the analyte. This technique may be used to obtain quantitative or semi-quantitative results. Some examples of such sandwich-type assays are described in. by U.S. Pat. No. 4,168,146 to Grubb, et al. and U.S. Pat. No. 4,366,241 to Tom, et al. An alternative technique is the "competitive-type" assay. In a "competitive-type" assay, the label is typically a labeled analyte or analyte-analogue that competes for binding of an antibody with any unlabeled analyte present in the sample. Competitive assays are typically used for detection of analytes such as haptens, each hapten being monovalent and capable of binding only one antibody molecule. Examples of competitive immunoassay devices are described in U.S. Pat. No. 4,235,601 to Deutsch. et al., U.S. Pat. No. 4,442,204 to Liotta, and U.S. Pat. No. 5,208,535 to Buechler, et al.

Despite the benefits achieved from these devices, many conventional lateral flow assays encounter significant inaccuracies when exposed to relatively high analyte concentrations. For example, when the analyte is present at high concentrations, a substantial portion of the analyte in the test sample may not form complexes with the conjugated probes. Thus, upon reaching the detection zone, the uncomplexed analyte competes with the complexed analyte for binding sites. Because the uncomplexed analyte is not labeled with a probe, it cannot be detected. Consequently, if a significant number of the binding sites become occupied by the uncomplexed analyte, the assay may exhibit a "false negative." This problem is commonly referred to as the "hook effect."

Various techniques for reducing the "hook effect" in immunoassays have been proposed. For instance, U.S. Pat. No. 6,184,042 to Neumann, et al. describes one technique for reducing the hook effect in a sandwich assay. The technique involves incubating the sample in the presence of a solid phase with at least two receptors capable of binding to the analyte. The first receptor is an oligomer of a binding molecule selected from antibodies, antibody fragments and mixtures thereof. The second receptor is bound to or capable of being bound to a solid phase. The use of a soluble oligomeric antibody is said to reduce the "hook effect."

A need still exists, however, for an improved technique of reducing the "hook effect" and extending the dynamic detection range of the assay device in an accurate, yet simple and cost-effective manner.

SUMMARY OF THE INVENTION

In accordance with one embodiment of the present invention, a flow-through assay device for detecting the presence or quantity of an analyte residing in a test sample is disclosed. The flow-through assay device comprises a porous membrane in communication with detection probes and defines a competitive zone and a detection zone. The competitive zone contains a first capture reagent that includes a first binding member immobilized on the porous membrane and a second binding member that is complexed to the first binding member. The second binding member is capable of producing a competitive signal when contained within the competitive zone. The detection zone contains a second capture reagent that is configured to bind to the detection probes or complexes thereof to produce a first detection signal. The second capture reagent is also configured to bind to the second binding member from the competitive zone to produce a second detection signal, wherein the amount of the analyte within the test sample is determined from the competitive signal, the first detection signal, the second detection signal, or combinations thereof.

In accordance with another embodiment of the present invention, a flow-through assay device for detecting the presence or quantity of an analyte residing in a test sample is disclosed. The flow-through assay device comprises a porous membrane in communication with optical detection probes conjugated with a first antibody specific for the analyte. The porous membrane defines a competitive zone and a detection zone. The competitive zone contains a second antibody immobilized on the porous membrane that is complexed to an antigen containing an optically detectable substance. The antigen is identical to or an analog of the analyte, and the optically detectable substance is capable of producing a competitive signal when contained within the competitive zone. The detection zone contains a third antibody that is configured to bind to complexes formed between the analyte and the conjugated optical detection probes to produce a first detection signal. The third antibody is also configured to bind to the antigen from the competitive zone to produce a second detection signal, wherein the amount of the analyte within the test sample is determined from the competitive signal, the first detection signal, the second detection signal, or combinations thereof.

In accordance with still another embodiment of the present invention, a method for detecting the presence or quantity of an analyte residing in a test sample is disclosed. The method comprises:

i) providing a flow-through assay device comprising a porous membrane in communication with detection probes conjugated with a first antibody specific for the analyte, the porous membrane defining:

a) a competitive zone within which is immobilized a second antibody complexed to an antigen containing an optically detectable substance, the antigen being identical to or an analog of the analyte and the optically detectable substance being capable of producing a competitive signal when contained within the competitive zone; and b) a detection zone within which a third antibody is immobilized that is configured to bind to complexes formed between the analyte and the conjugated optical detection probes to produce a first detection signal, the third antibody also being configured to bind to the antigen from the competitive zone to produce a second detection signal;

ii) contacting a test sample containing the analyte with the conjugated detection probes;

iii) measuring the intensity of the competitive signal at the competitive zone, and the intensity of the first and second detection signals at the detection zone; and iv) determining the amount of the analyte within the test sample from one or both of the following formulae:

$$D_1 + x,$$

when $x>0$, $D_1 = D_{1max}$ wherein, $x = C_{1max} - C_1$;

$C_{1max}$ is a predetermined maximum intensity for the competitive signal;

$C_1$ is the intensity of the competitive signal;

$D_1$ is the intensity of the first detection signal; and $D_{1max}$ is a predetermined maximum intensity for the first detection signal; or $$D_1 + D_2,$$

when $D_2 > 0$, $D_1 = D_{1max}$ wherein, $D_1$ is the intensity of the first detection signal;

$D_{1max}$ is a predetermined maximum intensity of the first detection signal; and $D_2$ is the intensity of the second detection signal.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which:

FIGS. 3A and 3B are graphical illustrations of the relationship between analyte concentration and signal intensities for the detection and competitive zones in accordance with one embodiment of the present invention, in which FIG. 3A illustrates the signal intensities for one label and FIG. 3B illustrates the signal intensities for another label;

Figure 1:
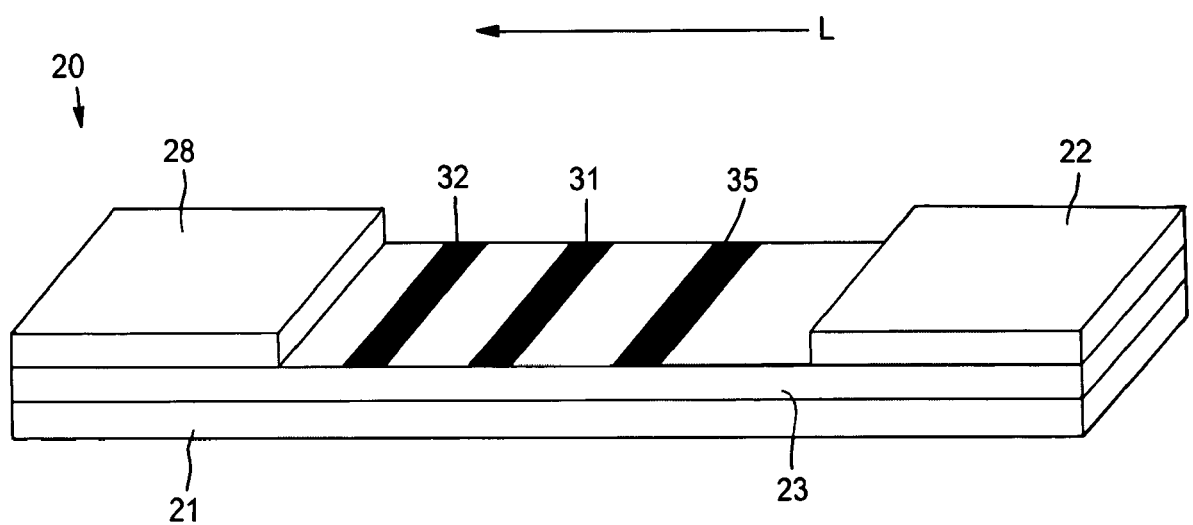
FIG. 1 is a perspective view of one embodiment of a flow-through assay device of the present invention.

Repeat use of reference characters in the present specification and drawings is intended to represent same or analogous features or elements of the invention.

DETAILED DESCRIPTION OF REPRESENTATIVE EMBODIMENTS

Definitions

As used herein, the term "analyte" generally refers to a substance to be detected. For instance, analytes may include antigenic substances, haptens, antibodies, and combinations thereof. Analytes include, but are not limited to, toxins, organic compounds, proteins, peptides, microorganisms, amino acids, nucleic acids, hormones, steroids, vitamins, drugs (including those administered for therapeutic purposes as well as those administered for illicit purposes), drug intermediaries or byproducts, bacteria, virus particles and metabolites of or antibodies to any of the above substances. Specific examples of some analytes include ferritin; creatinine kinase MB (CK-MB); digoxin; phenytoin; phenobarbitol; carbamazepine; vancomycin; gentamycin; theophylline; valproic acid; quinidine; luteinizing hormone (LH); follicle stimulating hormone (FSH); estradiol, progesterone; C-reactive protein; lipocalins; IgE antibodies; cytokines; vitamin B2 microglobulin; glycated hemoglobin (Gly. Hb); cortisol; digitoxin; N-acetylprocainamide (NAPA); procainamide; antibodies to rubella, such as rubella-IgG and rubella IgM; antibodies to toxoplasmosis, such as toxoplasmosis IgG (Toxo-IgG) and toxoplasmosis IgM (Toxo-IgM); testosterone; salicylates; acetaminophen; hepatitis B virus surface antigen (HBsAg); antibodies to hepatitis B core antigen, such as anti-hepatitis B core antigen IgG and IgM (Anti-HBC); human immune deficiency virus 1 and 2 (HIV 1 and 2); human T-cell leukemia virus 1 and 2 (HTLV); hepatitis B e antigen (HBeAg); antibodies to hepatitis B e antigen (Anti-HBe); influenza virus; thyroid stimulating hormone (TSH); thyroxine (T4); total triiodothyronine (Total T3); free triiodothyronine (Free T3); carcinoembryoic antigen (CEA); lipoproteins, cholesterol, and triglycerides; and alpha fetoprotein (AFP). Drugs of abuse and controlled substances include, but are not intended to be limited to, amphetamine; methamphetamine; barbiturates, such as amobarbital, secobarbital, pentobarbital, phenobarbital, and barbital; benzodiazepines, such as librium and valium; cannabinoids, such as hashish and marijuana; cocaine; fentanyl; LSD; methaqualone; opiates, such as heroin, morphine, codeine, hydromorphone, hydrocodone, methadone, oxycodone, oxymorphone and opium; phencyclidine; and propoxyhene. Other potential analytes may be described in U.S. Pat. No. 6,436,651 to Everhart, et al. and U.S. Pat. No. 4,366,241 to Tom et al.

As used herein, the term "test sample" generally refers to a material suspected of containing the analyte. The test sample may, for instance, include materials obtained directly from a source, as well as materials pretreated using techniques, such as, but not limited to, filtration, precipitation, dilution, distillation, mixing, concentration, inactivation of interfering components, the addition of reagents, and so forth. The test sample may be derived from a biological source, such as a physiological fluid, including, blood, interstitial fluid, saliva, ocular lens fluid, cerebral spinal fluid, sweat, urine, milk, ascites fluid, mucous, synovial fluid, peritoneal fluid, vaginal fluid, amniotic fluid or the like. Besides physiological fluids, other liquid samples may be used, such as water, food products, and so forth. In addition, a solid material suspected of containing the analyte may also be used as the test sample.

Detailed Description

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

In general, the present invention is directed to a flow-through assay device for detecting the presence or quantity of an analyte residing in a test sample. The device utilizes multiple detection zones, one of which is premised on "competitive" binding of the analyte and the other is premised on "sandwich" binding of the analyte. The present inventors believe that the combination of these zones may enable the detection of an analyte over extended concentration ranges.

Referring to FIG. 1, for instance, one embodiment of a flow-through assay device 20 that may be formed according to the present invention will now be described in more detail. As shown, the device 20 contains a porous membrane 23 optionally supported by a rigid material 21. In general, the porous membrane 23 may be made from any of a variety of materials through which the test sample is capable of passing. For example, the materials used to form the porous membrane 23 may include, but are not limited to, natural, synthetic, or naturally occurring materials that are synthetically modified, such as polysaccharides (e.g., cellulose materials such as paper and cellulose derivatives, such as cellulose acetate and nitrocellulose); polyether sulfone; polyethylene; nylon; polyvinylidene fluoride (PVDF); polyester; polypropylene; silica; inorganic materials, such as deactivated alumina, diatomaceous earth, $MgSO_4$, or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon or rayon); porous gels, such as silica gel, agarose, dextran, and gelatin; polymeric films, such as polyacrylamide; and the like. In one particular embodiment, the porous membrane 23 is formed from nitrocellulose and/or polyether sulfone materials. It should be understood that the term "nitrocellulose" refers to nitric acid esters of cellulose, which may be nitrocellulose alone, or a mixed ester of nitric acid and other acids, such as aliphatic carboxylic acids having from 1 to 7 carbon atoms.

The device 20 may also contain a wicking pad 28. The wicking pad 28 generally receives fluid that has migrated through the entire porous membrane 23. As is well known in the art, the wicking pad 28 may assist in promoting capillary action and fluid flow through the membrane 23.

To initiate the detection of an analyte within the test sample, a user may directly apply the test sample to a portion of the porous membrane 23 through which it may then travel in the direction illustrated by arrow "L" in FIG. 1. Alternatively, the test sample may first be applied to a sample pad (not shown) that is in fluid communication with the porous membrane 23. Some suitable materials that may be used to form the sample pad include, but are not limited to, nitrocellulose, cellulose, porous polyethylene pads, and glass fiber filter paper. If desired, the sample pad may also contain one or more assay pretreatment reagents, either diffusively or non-diffusively attached thereto.

In the illustrated embodiment, the test sample travels from the sample pad (not shown) to a conjugate pad 22 that is placed in communication with one end of the sample pad. The conjugate pad 22 is formed from a material through which the test sample is capable of passing. For example, in one embodiment, the conjugate pad 22 is formed from glass fibers. Although only one conjugate pad 22 is shown, it should be understood that multiple conjugate pads may also be used in the present invention.

To facilitate accurate detection of the presence or absence of an analyte within the test sample, a predetermined amount of detection probes are applied at various locations of the device 20. Any substance generally capable of producing a signal that is detectable visually or by an instrumental device may be used as detection probes. Various suitable substances may include calorimetric or fluorescent chromogens; catalysts; luminescent compounds (e.g., fluorescent, phosphorescent, etc.); radioactive compounds; visual labels, including colloidal metallic (e.g., gold) and non-metallic particles, dyed particles, hollow particles, enzymes or substrates, or organic polymer latex particles; liposomes or other vesicles containing signal producing substances; and so forth. For instance, some enzymes suitable for use as detection probes are disclosed in U.S. Pat. No. 4,275,149 to Litman, et al., which is incorporated herein in its entirety by reference thereto for all purposes. One example of an enzyme/substrate system is the enzyme alkaline phosphatase and the substrate nitro blue tetrazolium-5-bromo-4-chloro-3-indolyl phosphate, or derivative or analog thereof, or the substrate 4-methylumbelliferyl-phosphate. Other suitable detection probes may be described in U.S. Pat. No. 5,670,381 to Jou. et al. and U.S. Pat. No. 5,252,459 to Tarcha, et al., which are incorporated herein in their entirety by reference thereto for all purposes.

In some embodiments, the detection probes may contain a fluorescent compound that produces a detectable signal. The fluorescent compound may be a fluorescent molecule, polymer, dendrimer, particle, and so forth. Some examples of suitable fluorescent molecules, for instance, include, but are not limited to, fluorescein, europium chelates, phycobiliprotein, rhodamine and their derivatives and analogs. Generally speaking, fluorescence is the result of a three-stage process that occurs in certain fluorescent compounds. In the first stage, energy is supplied by an external source, such as an incandescent lamp or a laser and absorbed by the fluorescent compound, creating an excited electronic singlet state. In the second stage, the excited state exists for a finite time during which the fluorescent compound undergoes conformational changes and is also subject to a multitude of possible interactions with its molecular environment. During this time, the energy of the excited state is partially dissipated, yielding a relaxed state from which fluorescence emission originates. The third stage is the fluorescence emission stage wherein energy is emitted, returning the fluorescent compound to its ground state. The emitted energy is lower than its excitation energy (light or laser) and thus of a longer wavelength. This shift or difference in energy or wavelength allows the emission energy to be detected and isolated from the excitation energy.

Fluorescence detection generally utilizes wavelength filtering to isolate the emission photons from the excitation photons, and a detector that registers emission photons and produces a recordable output, usually as an electrical signal or a photographic image. There are various types of detectors, such as spectrofluorometers and microplate readers; scanners; microscopes; and flow cytometers. One suitable fluorescence detector for use with the present invention is a FluoroLog III Spectrofluorometer, which is sold by SPEX Industries, Inc. of Edison, N.J.

If desired, a technique known as "time-resolved fluorescence detection" may also be utilized in the present invention. Time-resolved fluorescence detection is designed to reduce background signals from the emission source or from scattering processes (resulting from scattering of the excitation radiation) by taking advantage of the fluorescence characteristics of certain fluorescent materials, such as lanthanide chelates of europium (Eu (III)) and terbium (Tb (III)). Such chelates may exhibit strongly red-shifted, narrow-band, long-lived emission after excitation of the chelate at substantially shorter wavelengths. Typically, the chelate possesses a strong ultraviolet absorption band due to a chromophore located close to the lanthanide in the molecule. Subsequent to light absorption by the chromophore, the excitation energy may be transferred from the excited chromophore to the lanthanide. This is followed by a fluorescence emission characteristic of the lanthanide. The use of pulsed excitation and time-gated detection, combined with narrow-band emission filters, allows for specific detection of the fluorescence from the lanthanide chelate only, rejecting emission from other species present in the sample that are typically shorter-lived or have shorter wavelength emission. Other time-resolved techniques for measuring fluorescence are described in U.S. Pat. No. 5,585,279 to Davidson and U.S. Pat. No. 5,637,509 to Hemmila, et al., which are incorporated herein in their entirety by reference thereto for all purposes.

The detection probes, such as described above, may be used alone or in conjunction with a particle (sometimes referred to as "beads" or "microbeads"). For instance, naturally occurring particles, such as nuclei, mycoplasma, plasmids, plastids, mammalian cells (e.g., erythrocyte ghosts), unicellular microorganisms (e.g., bacteria), polysaccharides (e.g., agarose), and so forth, may be used. Further, synthetic particles may also be utilized. For example, in one embodiment, latex particles that are labeled with a fluorescent or colored dye are utilized. Although any latex particle may be used in the present invention, the latex particles are typically formed from polystyrene, butadiene styrenes, styreneacrylicvinyl terpolymer, polymethylmethacrylate, polyethylmethacrylate, styrene-maleic anhydride copolymer, polyvinyl acetate, polyvinylpyridine, polydivinylbenzene, polybutyleneterephthalate, acrylonitrile, vinylchloride-acrylates, and so forth, or an aldehyde, carboxyl, amino, hydroxyl, or hydrazide derivative thereof. Other suitable particles may be described in U.S. Pat. No. 5,670,381 to Jou, et al. and U.S. Pat. No. 5,252,459 to Tarcha, et al., which are incorporated herein in their entirety by reference thereto for all purposes. Commercially available examples of suitable fluorescent particles include fluorescent carboxylated microspheres sold by Molecular Probes, Inc. under the trade names "FluoSphere" (Red 580/605) and "TransfluoSphere" (543/620), as well as "Texas Red" and 5- and 6-carboxytetramethylrhodamine, which are also sold by Molecular Probes, Inc. In addition, commercially available examples of suitable colored, latex microparticles include carboxylated latex beads sold by Bang's Laboratory, Inc.

When utilized, the shape of the particles may generally vary. In one particular embodiment, for instance, the particles are spherical in shape. However, it should be understood that other shapes are also contemplated by the present invention, such as plates, rods, discs, bars, tubes, irregular shapes, etc. In addition, the size of the particles may also vary. For instance, the average size (e.g., diameter) of the particles may range from about 0.1 nanometers to about 1,000 microns, in some embodiments, from about 0.1 nanometers to about 100 microns, and in some embodiments, from about 1 nanometer to about 10 microns. For instance, "micron-scale" particles are often desired. When utilized, such "micron-scale" particles may have an average size of from about 1 micron to about 1,000 microns, in some embodiments from about 1 micron to about 100 microns, and in some embodiments, from about 1 micron to about 10 microns. Likewise, "nano-scale" particles may also be utilized. Such "nano-scale" particles may have an average size of from about 0.1 to about 10 nanometers, in some embodiments from about 0.1 to about 5 nanometers, and in some embodiments, from about 1 to about 5 nanometers.

In some instances, it is desired to modify the detection probes in some manner so that they are more readily able to bind to the analyte. In such instances, the detection probes may be modified with certain specific binding members that are adhered thereto to form conjugated probes. Specific binding members generally refer to a member of a specific binding pair, i.e., two different molecules where one of the molecules chemically and/or physically binds to the second molecule. For instance, immunoreactive specific binding members may include antigens, haptens, aptamers, antibodies (primary or secondary), and complexes thereof, including those formed by recombinant DNA methods or peptide synthesis. An antibody may be a monoclonal or polyclonal antibody, a recombinant protein or a mixture(s) or fragment(s) thereof, as well as a mixture of an antibody and other specific binding members. The details of the preparation of such antibodies and their suitability for use as specific binding members are well known to those skilled in the art. Other common specific binding pairs include but are not limited to, biotin and avidin (or derivatives thereof), biotin and streptavidin, carbohydrates and lectins, complementary nucleotide sequences (including probe and capture nucleic acid sequences used in DNA hybridization assays to detect a target nucleic acid sequence), complementary peptide sequences including those formed by recombinant methods, effector and receptor molecules, hormone and hormone binding protein, enzyme cofactors and enzymes, enzyme inhibitors and enzymes, and so forth. Furthermore, specific binding pairs may include members that are analogs of the original specific binding member. For example, a derivative or fragment of the analyte, i.e., an analyte-analog, may be used so long as it has at least one epitope in common with the analyte.

Figure 2:
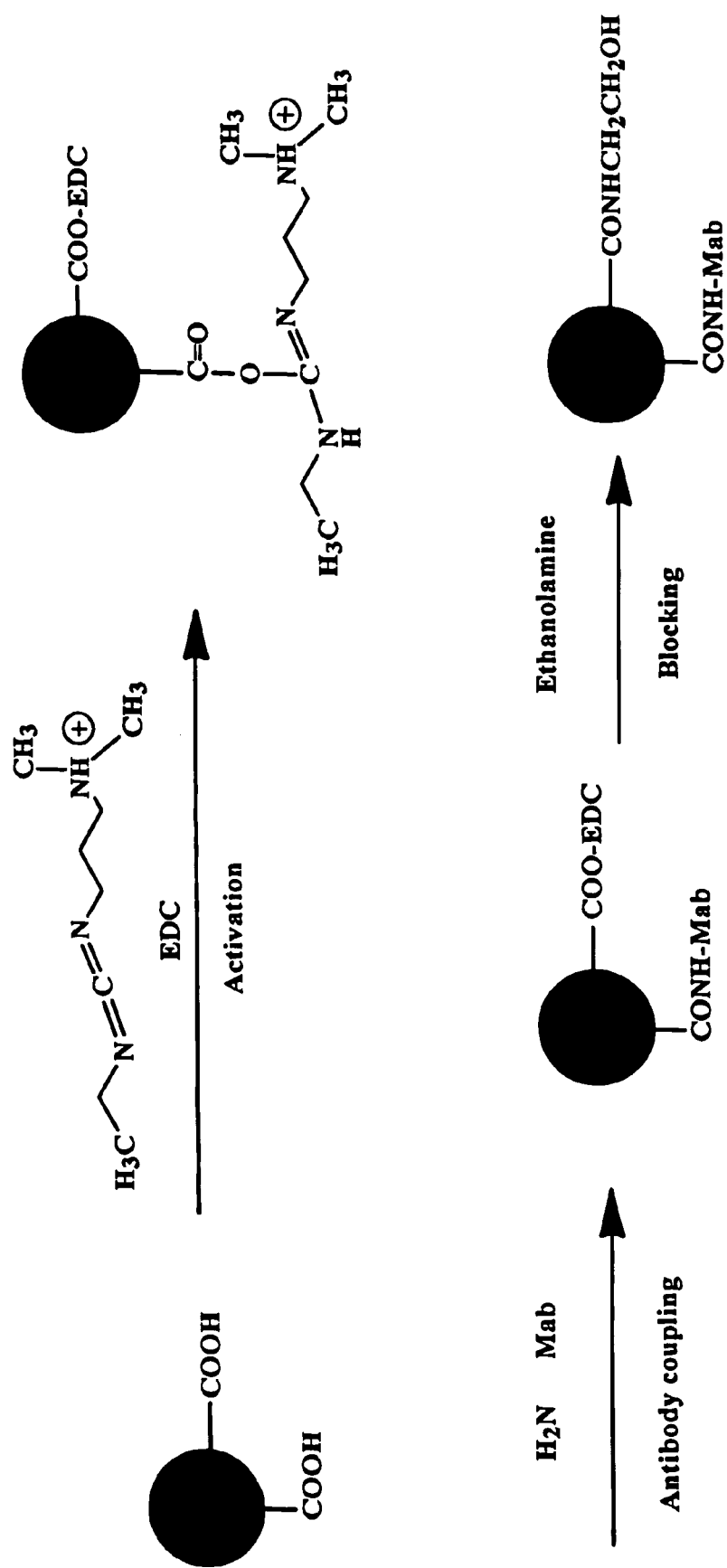
FIG. 2 is a graphical illustration of one embodiment for covalently conjugating an antibody to a detection probe.

The specific binding members may generally be attached to the detection probes using any of a variety of well-known techniques. For instance, covalent attachment of the specific binding members to the detection probes (e.g., particles) may be accomplished using carboxylic, amino, aldehyde, bromoacetyl, iodoacetyl, thiol, epoxy and other reactive or linking functional groups, as well as residual free radicals and radical cations, through which a protein coupling reaction may be accomplished. A surface functional group may also be incorporated as a functionalized co-monomer because the surface of the detection probe may contain a relatively high surface concentration of polar groups. In addition, although detection probes are often functionalized after synthesis, in certain cases, such as poly(thiophenol), the particles are capable of direct covalent linking with a protein without the need for further modification. For example, referring to FIG. 2, one embodiment of the present invention for covalently conjugating a particle-containing detection probe is illustrated. As shown, the first step of conjugation is activation of carboxylic groups on the probe surface using carbodiimide. In the second step, the activated carboxylic acid groups are reacted with an amino group of an antibody to form an amide bond. The activation and/or antibody coupling may occur in a buffer, such as phosphate-buffered saline (PBS) (e.g., pH of 7.2) or 2-(N-morpholino) ethane sulfonic acid (MES) (e.g., pH of 5.3). As shown, the resulting detection probes may then be blocked with ethanolamine, for instance, to block any remaining activated sites. Overall, this process forms a conjugated detection probe, where the antibody is covalently attached to the probe. Besides covalent bonding, other attachment techniques, such as physical adsorption, may also be utilized in the present invention.

Referring again to FIG. 1, the porous membrane 23 defines various zones configured to perform the assay. For instance, the porous membrane 23 defines a competitive zone 35 that contains a first capture reagent. The first capture reagent typically includes a first binding member immobilized on the porous membrane and a second binding member complexed to the first binding member. These first and second binding members may be selected from the same materials as the specific binding members described above, including, for instance, antigens, haptens, protein A or G, neutravidin, avidin, streptavidin, antibodies (e.g., polyclonal, monoclonal, etc.), and complexes thereof. To accomplish the desired competitive binding within the zone 35, it is generally desired that the second binding member include a molecule that is the identical to or an analog of the analyte to be detected. For example, in one embodiment, the first capture reagent includes an antigen identical to the analyte (i.e., second binding member). that is complexed to an antibody immobilized on the membrane 23 (i.e., first binding member). The second binding member is labeled with a substance capable of producing a signal that is detectable visually or by an instrumental device. Examples of such substances are generally described above. In one embodiment, for instance, an antigen is labeled with a fluorescent dye before being complexed to an immobilized antibody. In this manner, the competitive zone 35 is capable of producing a detectable signal, even when no analyte is present within the test sample.

The assay device 20 also contains a detection zone 31. Although not required, the detection zone 31 is typically positioned upstream from the competitive zone 35. A second capture reagent is immobilized within the detection zone 31. For example, in some embodiments, the second capture reagent may be a biological capture reagent such as described above. In one embodiment, for example, the second capture reagent is an antibody specific to the analyte. The second capture reagent serves as a stationary binding site for complexes formed between the analyte and the conjugated detection probes. Specifically, analytes, such as antibodies, antigens, etc., typically have two or more binding sites (e.g., epitopes). Upon reaching the detection zone 31, one of these binding sites is occupied by the specific binding member of the conjugated probe. However, the free binding site of the analyte may bind to the immobilized capture reagent. Upon being bound to the immobilized capture reagent, the complexed probes form a new ternary sandwich complex.

Although the detection zone 31 and competitive zone 35 provide accurate results, it is sometimes difficult to determine the relative concentration of the analyte within the test sample under actual test conditions. Thus, the assay device 20 may also include a calibration zone 32. In this embodiment, the calibration zone 32 is formed on the porous membrane 23 and is positioned downstream from the detection zone 31 and competitive zone 35. Alternatively, however, the calibration zone 32 may also be positioned upstream from the detection zone 31 and/or competitive zone 35.

The calibration zone 32 is provided with a third capture reagent that is capable of binding to calibration probes or uncomplexed detection probes that pass through the length of the membrane 23. When utilized, the calibration probes may be formed from the same or different materials as the detection probes. Generally speaking, the calibration probes are selected in such a manner that they do not bind to the first or second capture reagent at the detection zone 31 and competitive zone 35.

The third capture reagent of the calibration zone 32 may be the same or different than the capture reagents used in the detection zone 31 or competitive zone 35. For example, in one embodiment, the third capture reagent is a biological capture reagent. In addition, it may also be desired to utilize various non-biological materials for the third capture reagent of the calibration zone 32. The polyelectrolytes may have a net positive or negative charge, as well as a net charge that is generally neutral. For instance, some suitable examples of polyelectrolytes having a net positive charge include, but are not limited to, polylysine (commercially available from Sigma-Aldrich Chemical Co., Inc. of St. Louis, Mo.), polyethyleneimine; epichlorohydrin-functionalized polyamines and/or polyamidoamines, such as poly(dimethylamine-co-epichlorohydrin); polydiallyldimethyl-ammonium chloride; cationic cellulose derivatives, such as cellulose copolymers or cellulose derivatives grafted with a quaternary ammonium water-soluble monomer; and so forth. In one particular embodiment, CelQuat® SC-230M or H-100 (available from National Starch & Chemical, Inc.), which are cellulosic derivatives containing a quaternary ammonium water-soluble monomer, may be utilized. Moreover, some suitable examples of polyelectrolytes having a net negative charge include, but are not limited to, polyacrylic acids, such as poly(ethylene-co-methacrylic acid, sodium salt), and so forth. It should also be understood that other polyelectrolytes may also be utilized, such as amphiphilic polyelectrolytes (i.e., having polar and non-polar portions). For instance, some examples of suitable amphiphilic polyelectrolytes include, but are not limited to, poly(styryl-b-N-methyl 2-vinyl pyridinium iodide) and poly(styryl-b-acrylic acid), both of which are available from Polymer Source, Inc. of Dorval, Canada.

Although any polyelectrolyte may generally be used, the polyelectrolyte selected for a particular application may vary depending on the nature of the detection probes, the calibration probes, the porous membrane, and so forth. In particular, the distributed charge of a polyelectrolyte allows it to bind to substances having an opposite charge. Thus, for example, polyelectrolytes having a net positive charge are often better equipped to bind with probes that are negatively charged, while polyelectrolytes that have a net negative charge are often better equipped to bind to probes that are positively charged. Thus, in such instances, the ionic interaction between these molecules allows the required binding to occur within the calibration zone 32. Nevertheless, although ionic interaction is primarily utilized to achieve the desired binding in the calibration zone 32, polyelectrolytes may also bind with probes having a similar charge.

Because the polyelectrolyte is designed to bind to probes, it is typically desired that the polyelectrolyte be substantially non-diffusively immobilized on the surface of the porous membrane 23. Otherwise, the probes would not be readily detectable by a user. Thus, the polyelectrolytes may be applied to the porous membrane 23 in such a manner that they do not substantially diffuse into the matrix of the porous membrane 23. In particular, the polyelectrolytes typically form an ionic and/or covalent bond with functional groups present on the surface of the porous membrane 23 so that they remain immobilized thereon. Although not required, the formation of covalent bonds between the polyelectrolyte and the porous membrane 23 may be desired to more permanently immobilize the polyelectrolyte thereon. For example, in one embodiment, the monomers used to form the polyelectrolyte are first formed into a solution and then applied directly to the porous membrane 23. Various solvents (e.g., organic solvents, water, etc.) may be utilized to form the solution. Once applied, the polymerization of the monomers is initiated using heat, electron beam radiation, free radical polymerization, and so forth. In some instances, as the monomers polymerize, they form covalent bonds with certain functional groups of the porous membrane 23, thereby immobilizing the resulting polyelectrolyte thereon. For example, in one embodiment, an ethyleneimine monomer may form a covalent bond with a carboxyl group present on the surface of some porous membranes (e.g., nitrocellulose).

In another embodiment, the polyelectrolyte may be formed prior to application to the porous membrane 23. If desired, the polyelectrolyte may first be formed into a solution using organic solvents, water, and so forth. Thereafter, the polyelectrolytic solution is applied directly to the porous membrane 23 and then dried. Upon drying, the polyelectrolyte may form an ionic bond with certain functional groups present on the surface of the porous membrane 23 that have a charge opposite to the polyelectrolyte. For example, in one embodiment, positively-charged polyethyleneimine may form an ionic bond with negatively-charged carboxyl groups present on the surface of some porous membranes (e.g., nitrocellulose).

In addition, the polyelectrolyte may also be crosslinked to the porous membrane 23 using various well-known techniques. For example, in some embodiments, epichlorohydrin-functionalized polyamines and/or polyamidoamines may be used as a crosslinkable, positively-charged polyelectrolyte. Examples of these materials are described in U.S. Pat. No. 3,700,623 to Keim and U.S. Pat. No. 3,772,076 to Keim, U.S. Pat. No. 4,537,657 to Keim, which are incorporated herein in their entirety by reference thereto for all purposes and are believed to be sold by Hercules, Inc., Wilmington, Del. under the Kymene™ trade designation. For instance, Kymene™ 450 and 2064 are epichlorohydrin-functionalized polyamine and/or polyamidoamine compounds that contain epoxide rings and quaternary ammonium groups that may form covalent bonds with carboxyl groups present on certain types of porous membranes (e.g., nitrocellulose) and crosslink with the polymer backbone of the porous membrane when cured. In some embodiments, the crosslinking temperature may range from about 50° C. to about 120° C. and the crosslinking time may range from about 10 to about 600 seconds.

Although various techniques for non-diffusively immobilizing polyelectrolytes on the porous membrane 23 have been described above, it should be understood that any other technique for non-diffusively immobilizing polyelectrolytic compounds may be used in the present invention. In fact, the aforementioned methods are only intended to be exemplary of the techniques that may be used in the present invention. For example, in some embodiments, certain components may be added to the polyelectrolyte solution that may substantially inhibit the diffusion of such polyelectrolytes into the matrix of the porous membrane 23.

Thus, the calibration zone 32 may be used to calibrate the various signal intensities of the detection zone 31 and competitive zone 35 under different assay conditions. For example, the detection and calibration signals may be plotted versus analyte concentration for a range of known analyte concentrations to generate a calibration curve. To determine the quantity of analyte in an unknown test sample, the signal ratio may then be converted to analyte concentration according to the calibration curve. It should be noted that any appropriate mathematical relationship may be plotted versus the analyte concentration to generate the calibration curve.

The detection zone 31, competitive zone 35, and calibration zone 32 may each provide any number of distinct detection regions so that a user may better determine the concentration of a particular analyte within a test sample. Each region may contain the same capture reagents, or may contain different capture reagents. For example, the zones may include two or more distinct regions (e.g., lines, dots, etc.). The regions may be disposed in the form of lines in a direction that is substantially perpendicular to the flow of the test sample through the assay device 20. Likewise, in some embodiments, the regions may be disposed in the form of lines in a direction that is substantially parallel to the flow of the test sample through the assay device 20.

Although various embodiments of device configurations have been described above, it should be understood, that a device of the present invention may generally have any configuration desired, and need not contain all of the components described above. Various other device configurations, for instance, are described in U.S. Pat. No. 5,395,754 to Lambotte, et al.; U.S. Pat. No. 5,670,381 to Jou et al.; and U.S. Pat. No. 6,194,220 to Malick, et al., which are incorporated herein in their entirety by reference thereto for all purposes.

Figure 4:
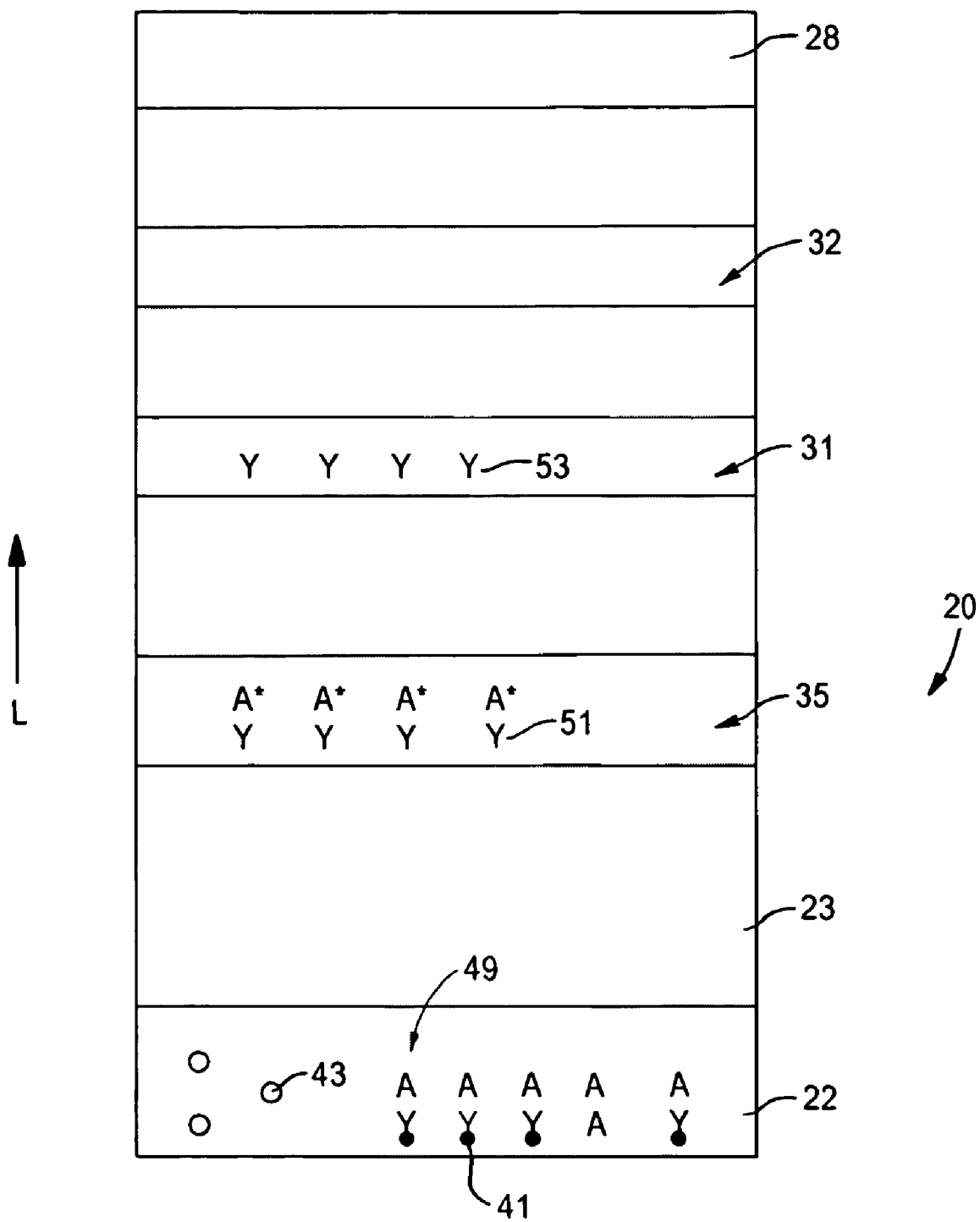
FIG. 4 is a schematic illustration of the mechanism used for one embodiment of the present invention prior to performance of the assay.
Figure 5:
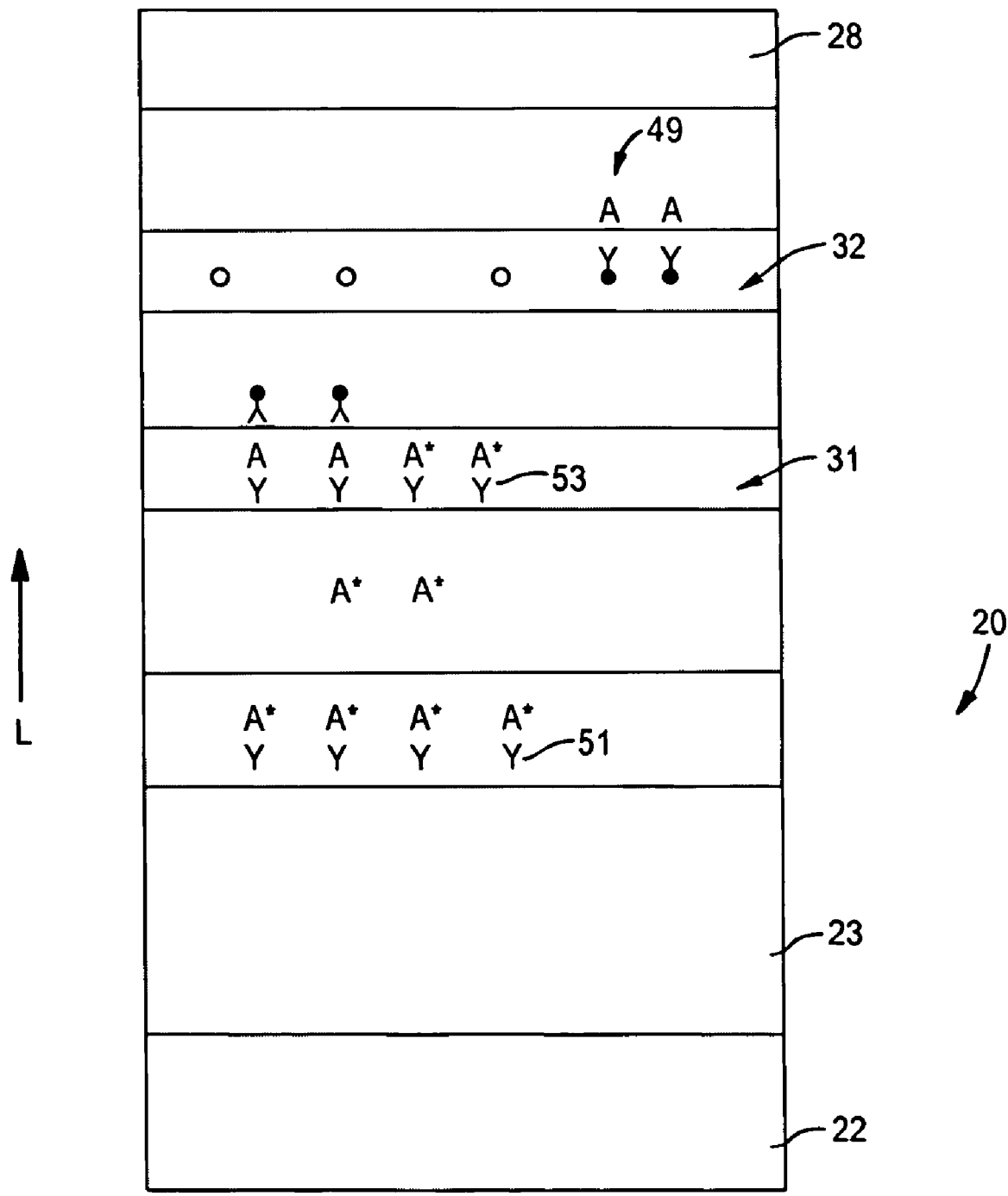
FIG. 5 illustrates the embodiment of FIG. 4 after completion of the assay.

Regardless of their particular configuration of the assay device 20, the competitive zone 35 and detection zone 31 function in tandem to improve the analyte detection range. Referring to FIGS. 4-5, one embodiment of a method for detecting the presence of an excess concentration of antigen using fluorescent detection techniques will now be described in more detail. Initially, as shown in FIG. 4, a test sample containing an antigen A is applied to the sample pad (not shown) and travels in the direction "L" to the conjugate pad 22, where the analyte A mixes with fluorescent detection probes 41 conjugated with an antibody and fluorescent calibration probes 43 (may or may not be conjugated). Although the use of fluorescence is utilized in this particular embodiment, it should be understood that other optical detection techniques, such as phosphorescence, reflectance, etc., are equally suitable for use in the present invention. For example, in one embodiment, as is well known in the art, a reflectance spectrophotometer or reader may be utilized to detect the presence of probes that exhibit a visual color (e.g. dyed latex particles). One suitable reflectance reader is described, for instance, in U.S. Patent App. Pub. No. 2003/0119202 to Kaylor, et al., which is incorporated herein in its entirety by reference thereto for all purposes.

In the embodiment illustrated in FIG. 4, the antigen A binds with the conjugated fluorescent detection probes 41 to form analyte/conjugated probe complexes 49. As indicated, some of the antigen A remains free due to the limited availability of the conjugated detection probes 41. As shown in FIG. 5, the free antigen A and the complexes 49 then travel to the competitive zone 35, within which is immobilized an antibody 51 complexed to a labeled molecule A* that is identical in nature to the antigen A. Due to its smaller size, the free antigen A reaches the competitive zone 35 first, and competes with the molecule A* for the binding sites on the antibody 51. The complexes 49 and the displaced molecules A* travel on to the detection zone 31 and bind to an antibody 53. Finally, the fluorescent calibration probes 43 travel through both the detection zone 31 and competitive zone 35 to bind with polyelectrolyte (not shown) at the calibration zone 32.

Once captured, the fluorescence signals of the labeled molecules A* and detection probes 41 may be measured at the detection zone 31 and the competitive zone 35. Ideally, the emission wavelength of the fluorescent compound used for the antigen A* is different than the emission wavelength used for the detection probes 41. In this manner, the respective signals may be easily distinguished from each other within the same zone. In addition, the fluorescent signal of the calibration probes 42 may also be measured at the calibration zone 32. The absolute amount of the analyte may be ascertained by comparing the fluorescence signals at the detection zone 31 with the fluorescence signals at the competitive zone 35, and optionally with the fluorescent signal at the calibration zone 32.

Figure 3A:
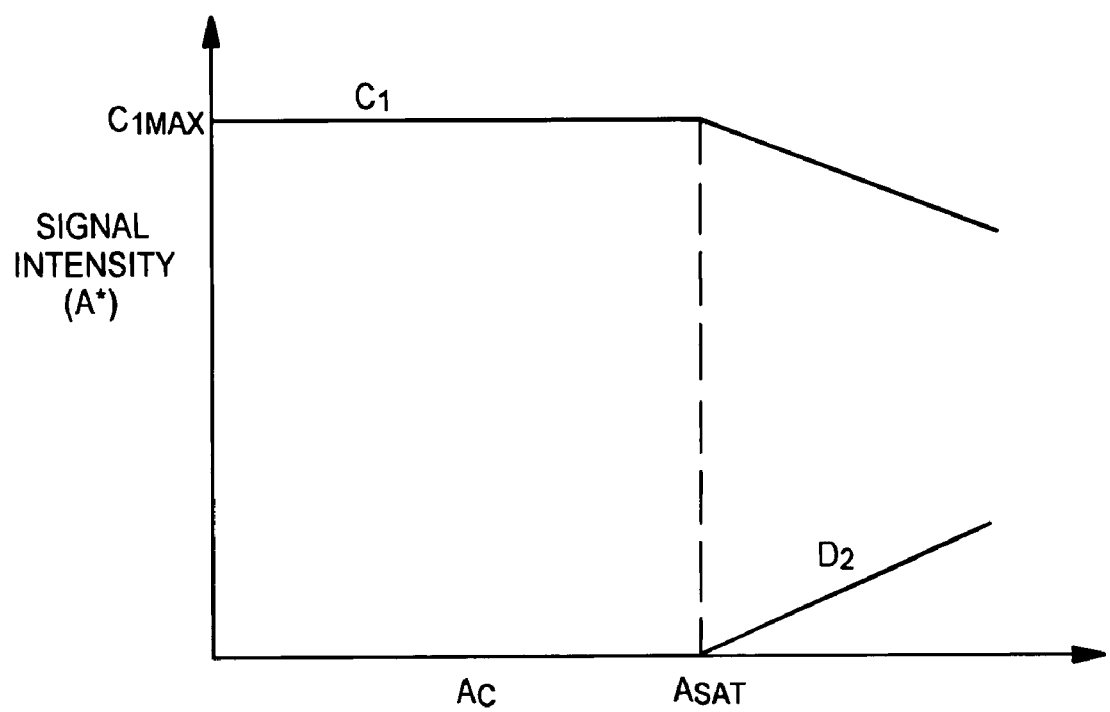
Figure 3B:
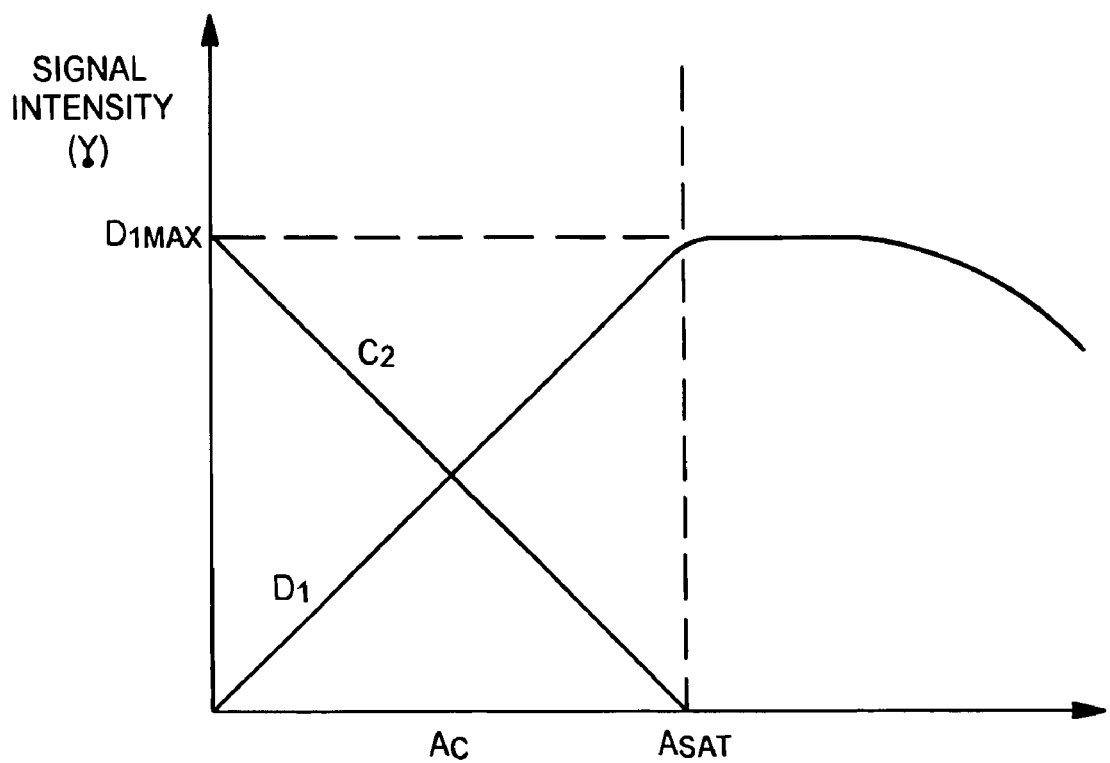

The ability to utilize different signal intensities to determine analyte concentration is illustrated graphically in FIGS. 3A and 3B. It should be understood that the signal intensities do not necessarily have to follow the illustrated relationship, and that this relationship is given for exemplary purposes only. In this regard, FIGS. 3A and 3B show the relationship of the signal intensity of the fluorescent detection labels of FIGS. 4 and 5 (A* and the detection probes 41) for both the competitive zone 35 and the detection zone 31. As shown, when no analyte A is present in the test sample, the labeled antigen A* produces a first competitive signal ("$C_1$") at the competitive zone 35 that is constant at its maximum value, $C_{1max}$. Further, the conjugated detection probes 41 bind to the antigen A* within the competitive zone 35, thus producing a second competitive signal ("$C_2$"). No signals exist at the detection zone 31.

As the concentration of the analyte A increases, it begins to form the complexes 49 with the conjugated detection probes 41. Because the complexes 49 no longer possess an epitope capable of binding with the antigen A*, they travel past the competitive zone 35 and bind to the antibody 53 at the detection zone 31. This causes a decrease in the second competitive signal "$C_2$", and also causes the production of a first detection signal "$D_1$" at the detection zone 31. The intensity of the second competitive signal "$C_2$" continues to decrease and the intensity of the first detection signal "$D_1$" continues to increase until the concentration of the analyte A exceeds the amount of available conjugated detection probes 41, which is designated in FIGS. 3A and 3B as "$A_{sat}$."

At "$A_{sat}$", the free analyte A travels to the competitive zone 35. Because it is generally smaller in size, the free analyte A typically reaches the competitive zone 35 before the complexes 49. Thus, within the competitive zone 35, the free analyte A begins to compete with the labeled antigen A* for the binding site of the antibody 51. Specifically, the complex formed between the antigen A* and the antibody 51 is not covalent, but instead based one more temporary and reversible types of bonds, such as hydrogen bonds, electrostatic bonds, van der Waals forces, hydrophobic bonds, and so forth. For example, antigen/antibody complexing is generally based on the following equilibrium reaction:

Antigen+Antibody←→Complex

The affinity of an antibody for a corresponding antigen is thus based on the equilibrium constant, k, for the antibody/antigen pair. Although the affinity is generally high, the existence of equilibrium still dictates that the antigen of the complex is replaceable.

Without intending to be limited by theory, the present inventors believe that this ability to replace the antigen A* with the free analyte A from the test sample may help extend the detection range of the assay. Namely, when the free analyte A begins to compete with the antigen A* for binding sites at the competitive zone 35, the intensity of the first competitive signal "$C_1$" begins to decrease due to a loss in the labeled antigen A* (FIG. 3A). This decrease is proportional to the amount of analyte A exceeding the analyte saturation concentration "$A_{sat}$" and the binding capacity of the conjugated detection probes 41. Moreover, at the analyte saturation concentration "$A_{sat}$", the intensity of the second competitive signal "$C_2$" is zero as all of the available conjugated detection 41 probes are used to form the complexes 49, and thus, bypass the competitive zone 35 (FIG. 3B).

Further, at the analyte saturation concentration "$A_{sat}$", all of the conjugated detection probes 41 form complexes 49 that ultimately bind to the detection zone 31. Thus, the intensity of the first detection signal "$D_1$" reaches its maximum value, designated "$D_{1max}$". This value is predetermined and known because the amount of the detection probes 41 is selected to correspond to the amount of the available antibody 53 at the detection zone 31. Although the first detection signal "$D_1$" reaches its maximum intensity at the analyte saturation concentration "$A_{sat}$", a second detection signal "$D_2$" begins to be produced. This second detection signal "$D_2$" is a result of the labeled antigen A* being replaced at the competitive zone 35 and traveling to the detection zone 31, where it and the conjugated detection probes 41 become immobilized. In this manner, the second detection signal "$D_2$" increases, while the first detection signal "$D_1$" actually decreases. In most instances, the signal "$D_2$" should also be proportional to the difference in the signals "$C_{1max}$" and "$C_1$." It should be also understood that, due to the equilibrium conditions at the competitive zone 35, a small portion of free analyte A from the test sample may bind at the detection zone 31. Although this free analyte A is not detectable, it is believed to be insignificant in comparison to the amount of free analyte A that would otherwise be present in the absence of the competitive zone 35.

Thus, in accordance with the present invention, the analyte concentration within the test sample may be used by measuring the detection signals at the competitive zone 35 and/or the detection zone 31. In one embodiment, the analyte concentration is determined from (e.g., directly or indirectly proportional to) the following formula:

$$D_1+x,$$

when $x>0$, $D_1=D_{1max}$ wherein, $x=C_{1max}-C_1$;

$C_{1max}$ is a predetermined maximum intensity of the first competitive signal, determined in the absence of an analyte;

$C_1$ is the measured intensity of the first competitive signal;

$D_1$ is the measured intensity of the first detection signal; and $D_{1max}$ is a predetermined maximum intensity of the first detection signal.

Moreover, because the signal "$D_2$" should also be proportional to the difference in the signals "$C_{1max}$" and "$C_1$", the analyte concentration may alternatively be determined from (e.g., directly or indirectly proportional to) the following formula:

$$D_1+D_2,$$

when $D_2>0$, $D_1=D_{1max}$ wherein, $D_1$ is the measured intensity of the first detection signal;

$D_{1max}$ is a predetermined maximum intensity of the first detection signal; and $D_2$ is the measured intensity of the second detection signal.

Thus, for analyte concentrations less than or equal to the saturation concentration "$A_{sat}$", $x=D_2=0$ so that the analyte concentration is determined only from the intensity of the signal "$D_1$". For analyte concentrations greater than "$A_{sat}$", x or $D_2>0$ so that the analyte concentration is determined from the sum of "$D_{1max}$" and x or $D_2$. It should be understood that other mathematical relationships between $D_1$, $D_2$, and x may also be utilized in the present invention, as would readily be understood by those skilled in the art. Regardless of the mathematical relationship utilized, the present inventors believe that the use of competitive and detection zones may enable the detection of an analyte over extended concentration ranges in a simple, efficient, and cost-effective manner.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A flow-through assay device for detecting the presence or quantity of an analyte residing in a test sample, said flow-through assay device comprising a porous membrane in communication with optical detection probes conjugated with a first antibody specific for the analyte, said porous membrane defining:
  a competitive zone that contains a second antibody immobilized on said porous membrane that is complexed to an antigen containing an optically detectable substance prior to the application of a test sample to the device, said antigen being identical to or an analog of the analyte and said optically detectable substance being capable of producing a competitive signal when contained within said competitive zone; and
  a detection zone within which a third antibody is immobilized that is configured to bind to complexes formed between the analyte and said conjugated optical detection probes to produce a first detection signal, said third antibody also being configured to bind to said antigen from said competitive zone to produce a second detection signal, wherein the amount of the analyte within the test sample is determined from said competitive signal, and at least one of said first detection signal and said second detection signal.

2. A flow-through assay device as defined in claim 1, wherein said optical detection probes and said optically detectable substance of said antigen each comprise a visual label.

3. A flow-through assay device as defined in claim 1, wherein said optical detection probes and said optically detectable substance of said antigen each comprise a luminescent compound.

4. A flow-through assay device as defined in claim 3, wherein said detection probes emit a signal at a different wavelength than said optically detectable substance of said antigen.

5. A flow-through assay device as defined in claim 1, wherein said porous membrane further defines a calibration zone that is configured to produce a calibration signal.

6. A flow-through assay device as defined in claim 1, wherein the amount of the analyte within the test sample is capable of being determined from one or both of the following formulae:

$$D_1 + x,$$

when $x > 0$, $D_1 = D_{1max}$ wherein,
$x = C_{1max} - C_1$;
$C_{1max}$ is a predetermined maximum intensity for said competitive signal;
$C_1$ is the intensity of said competitive signal;
$D_1$ is the intensity of said first detection signal; and
$D_{1max}$ is a predetermined maximum intensity for said first detection signal; or $$D_1 + D_2,$$

when $D_2 > 0$, $D_1 = D_{1max}$ wherein,
$D_1$ is the intensity of said first detection signal;
$D_{1max}$ is a predetermined maximum intensity for said first detection signal; and
$D_2$ is the intensity of said second detection signal.

7. A flow-through assay device as defined in claim 1, wherein the intensity of the competitive signal is at a maximum value when no analyte is present within the test sample.

8. A flow-through assay device as defined in claim 1, wherein the conjugated detection probes bind to the antigen within the competitive zone to produce a second competitive signal when no analyte is present within the test sample.

9. A flow-through assay device as defined in claim 1, wherein the intensity of the first detection signal reaches a maximum value at or near the saturation concentration of the analyte within the test sample.

* * * * *